US008679799B2

(12) United States Patent
Wach et al.

(10) Patent No.: US 8,679,799 B2
(45) Date of Patent: Mar. 25, 2014

(54) PRODUCTION OF ACID AND SOLVENT IN MICROORGANISMS

(75) Inventors: Wolfgang Wach, Worms (DE); Karsten Harms, Worms (DE); Michael Klingeberg, Gruenstadt (DE); Peter Duerre, Ulm (DE); Niklas Nold, Biberach (DE); Bettina Schiel, Ulm (DE)

(73) Assignee: Sudzucker Aktiengesellschaft Mannheim/Ochsenfurt, Mannheim (DE)

( * ) Notice: Subject to any disclaimer, the term of this patent is extended or adjusted under 35 U.S.C. 154(b) by 182 days.

(21) Appl. No.: 13/140,398

(22) PCT Filed: Dec. 15, 2009

(86) PCT No.: PCT/EP2009/008961
§ 371 (c)(1),
(2), (4) Date: Jun. 16, 2011

(87) PCT Pub. No.: WO2010/069542
PCT Pub. Date: Jun. 24, 2010

(65) Prior Publication Data
US 2011/0281313 A1 Nov. 17, 2011

(30) Foreign Application Priority Data
Dec. 20, 2008 (DE) .................... 10 2008 064 249

(51) Int. Cl.
| C12P 7/40 | (2006.01) |
| C12P 7/16 | (2006.01) |
| C12N 9/00 | (2006.01) |
| C12N 9/04 | (2006.01) |
| C12N 1/20 | (2006.01) |
| C12N 15/00 | (2006.01) |
| C12N 15/74 | (2006.01) |
| C07H 21/04 | (2006.01) |

(52) U.S. Cl.
USPC .......... 435/136; 435/160; 435/183; 435/190; 435/252.3; 435/320.1; 435/471; 536/23.2

(58) Field of Classification Search
None
See application file for complete search history.

(56) References Cited

FOREIGN PATENT DOCUMENTS

WO WO-2009/082148 A2 7/2009

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Feustel et al. Appl Environ Microbiol. Feb. 2004;70(2):798-80.*
Accession L14817. Jan. 13, 1999.*
Nold, N.: "Untersuchungen zur Regulation des sol-Operons in *Clostridium acetobutylicum*" [Online] Oct. 23, 2008, XP007911947 Retrieved from the Internet: URL:http://vts.uni-ulm.de/docs/2008/6544/vts_6544_8915.pdf> [retrieved on Feb. 26, 2010].
Thormann, K., et al: "Orf5/SoIR: a transcriptional repressor of the sol operon of *Clostridium acetobutylicum* ?" Journal of Industrial Microbiology & Biotechnology, Nov. 2001, vol. 27, No. 5, Nov. 2001, pp. 307-313, XP009130150, ISSN: 1367-5435.
Fischer, R. J., et al.: "Cloning, sequencing, and molecular analysis of the sol operon of *Clostridium acetobutylicum*, a chromosomal locus involved in solventogenesis," Journal of Bacteriology, Nov 1993, vol. 175, No. 21, Nov. 1993, pp. 6959-6969, XP009130152, ISSN: 0021-9193.
Tummala Seshu B., et al., "Design of antisense RNA constructs for downregulation of the acetone formation pathway of *Clostridium acetobutylicum*," Journal of Bacteriology, American Society for Microbiology, US, vol. 185, No. 6, Mar. 1, 2003, pp. 1923-1934, XP002443072, ISSN: 0021-9193.
Chen Y., et al., "Computational Identification of Small RNAs in *Clostridium Acetobutylicum* and Prediction of mRNA Targets," [Online] Nov. 19, 2008, XP002570526, Annual Meeting AICHE 2008, Retrieved from the Internet: URL:http://www.nt.ntnu.no/users/skoge/prost/proceedings/aiche-2008/data/papers/P128006.pdf> [retrieved on Feb. 25, 2010].
Chen Y., et al.: "Abstract: Computational Identification of Small RNAs in *Clostridium Acetobutylicum* and Prediction of mRNA Targets," [Online] Nov. 19, 2008, XP002570527, Aiche 2008, Retrieved from the Internet: URL:http://aiche.confex.com/aiche/2008/techprogram/P128006.HTM> [retrieved on Feb. 25, 2010].
-& Anonymous: "Session 482—In Silico Systems Biology II (TA000)" [Online] Nov. 19, 2008, XP002570528, AICHE 2008, Retrieved from the Internet: URL:http://aiche.confex.com/aiche/2008/techprogram/S8984.HTM> [retrieved on Nov. 25, 2008].
Tummala Seshu B., et al.: "Antisense RNA downregulation of coenzyme A transferase combined with alcohol-aldehyde dehydrogenase overexpression leads to predominantly alcohologenic *Clostridium acetobutylicum* fermentations," Journal of Bacteriology, American Society for Microbiology, US, vol. 185, No. 12, Jun. 1, 2003, pp. 3644-3653, XP002556652, ISSN: 0021-9193.
Desai Ruchir P., et al.: "Antisense RNA strategies for metabolic engineering of *Clostridium acetobutylicum*," Applied and Environmental Microbiology, American Society for Microbiology, US, vol. 65, No. 3, Mar. 1, 1999, pp. 936-945, XP002443073, ISSN: 0099-2240.
Papoutsakis, et al.: "Engineering solventogenic clostridia," Current Opinion in Biotechnology, London, GB, vol. 19, No. 5, Oct. 1, 2008, pp. 420-429, XP025495863, ISSN: 0958-1669 [retrieved on Sep. 13, 2008].

(Continued)

*Primary Examiner* — Christian Fronda
(74) *Attorney, Agent, or Firm* — Harness, Dickey & Pierce, P.L.C.

(57) ABSTRACT

The invention relates to a method and means for the bioengineered fermentative production of solvents, in particular of butanol, acetone and ethanol, and of short-chained carboxylic acids such as acetic acid and butyric acid, in particular in host cells of the species *Clostridium*. The invention provides new methods and means for regulating the expression of the enzyme activities involved in acid production and or solvent production of the host cell.

16 Claims, 13 Drawing Sheets

(56) References Cited

OTHER PUBLICATIONS

DÄrre Peter, et al.: "Transcriptional regulation of solventogenesis in *Clostridium acetobutylicum* ," Journal of Molecular Microbiology and Biotechnology, May 2002, vol. 4, No. 3, May 2002, pp. 295-300, XP009130157, ISSN: 1464-1801.

Database Geneseq [Online] Aug. 20, 2009, "C. acetobutylicum adhE1/ctfAB gene isolating PCR primer P1/SalI SEQ ID: 1.", XP002570530, retrieved from EBI accession No. GSN:AXF05051, Database accession No. AXF05051.

Thormann, Kai, et al.: "Control of Butanol Formation in *Clostridium acetobutylicum* by Transcriptional Activation," Journal of Bacteriology, Apr. 2002, p. 1966-1973.

Nair, R. V., et al.: "Regulation of the sol Locus Genes for Butanol and Acetone Formation in *Clostridium acetobutylicum* ATCC 824 by a Putative Transcriptional Repressor," Journal of Bacteriology, Jan. 1999, p. 319-330.

English Translation of the International Preliminary Report on Patentability, IB, Geneva, issued Jun. 21, 2011, incorporating the English Translation of the Written Opinion of the ISA.

* cited by examiner

SEQUENCE LISTING

<160> NUMBER OF SEQ ID NOS: 16

<210> SEQ ID NO 1
<211> LENGTH: 209
<212> TYPE: DNA
<213> ORGANISM: Clostridium botulinum

<400> SEQUENCE: 1

```
ttcagaagtc tacaaattaa gtttatattt agaccctggg gtgtaactat agtatttaat      60
attggtacta ttaattaggg ttatatatac tagaacttat catggtaaac ataaatataa     120
actcaattct atttatgctc ctataaaatt ttataatata ggaaaactgc taaatgtaaa     180
ttatacgttt acatttagca gtttattt                                        209
```

<210> SEQ ID NO 2
<211> LENGTH: 180
<212> TYPE: DNA

<213> ORGANISM: Clostridium botulinum

<400> SEQUENCE: 2

| tagaccctgg ggtgtaacta tagtatttaa tattggtact attaattagg gttatatata | 60 |
| ctagaactta tcatggtaaa cataaatata aactcaattc tatttatgct cctataaaat | 120 |
| tttataatat aggaaaactg ctaaatgtaa attatacgtt tacatttagc agtttatttt | 180 |

<210> SEQ ID NO 3
<211> LENGTH: 137
<212> TYPE: DNA
<213> ORGANISM: Clostridium botulinum

<400> SEQUENCE: 3

| tagaccctgg ggtgtaacta tagtatttaa tattggtact attaattagg gttatatata | 60 |
| ctagaactta tcatggtaaa cataaatata aactcaattc tatttatgct cctataaaat | 120 |
| tttataatat aggaaaa | 137 |

<210> SEQ ID NO 4
<211> LENGTH: 211
<212> TYPE: DNA
<213> ORGANISM: Clostridium botulinum

<400> SEQUENCE: 4

| tatgtagacc ctggggtgta actatagtat ttaatattgg tactattaat tagggttata | 60 |
| tatactagaa cttatcatgg taaacataaa tataaactca attctattta tgctcctata | 120 |
| aaattttata ataggaaa actgctaaat gtaaattata cgtttacatt tagcagttta | 180 |
| ttttaaacct tcatattttt ctaaatatac a | 211 |

<210> SEQ ID NO 5
<211> LENGTH: 254
<212> TYPE: DNA
<213> ORGANISM: Clostridium botulinum

<400> SEQUENCE: 5

| tccttaagat atagcttctt ttatgtagta ttatttcaga agtctacaaa ttaagtttat | 60 |
| atttagaccc tggggtgtaa ctatagtatt taatattggt actattaatt agggttatat | 120 |
| atactagaac ttatcatggt aaacataaat ataaactcaa ttctatttat gctcctataa | 180 |
| aattttataa ataggaaaa ctgctaaatg taaattatac gtttacattt agcagtttat | 240 |
| tttaaacctt catg | 254 |

<210> SEQ ID NO 6
<211> LENGTH: 254
<212> TYPE: DNA
<213> ORGANISM: Clostridium botulinum

<400> SEQUENCE: 6

| tccttaagat atagcttctt ttatgtagta ttatttcaga agtctacaaa ttaagtttat | 60 |
| attttttcct atattataaa attttatagg agcataaata gaattgagtt tatatttatg | 120 |
| tttaccatga taagttctag tatatataac cctaattaat agtaccaata ttaaatacta | 180 |
| tagttacacc ccagggtcta ctgctaaatg taaattatac gtttacattt agcagtttat | 240 |
| tttaaacctt catg | 254 |

<210> SEQ ID NO 7
<211> LENGTH: 75
<212> TYPE: DNA

-continued

<213> ORGANISM: Clostridium botulinum

<400> SEQUENCE: 7
ttttcctata ttataaaatt ttataggagc ataaatagaa ttgagtttat atttatgttt    60
accatgataa gttct                                                    75

<210> SEQ ID NO 8
<211> LENGTH: 115
<212> TYPE: DNA
<213> ORGANISM: Clostridium botulinum

<400> SEQUENCE: 8
ttttcctata ttataaaatt ttataggagc ataaatagaa ttgagtttat atttatgttt    60
accatgataa gttctagtat atataaccct aattaatagt accaatatta aatac         115

<210> SEQ ID NO 9
<211> LENGTH: 72
<212> TYPE: DNA
<213> ORGANISM: Clostridium botulinum

<400> SEQUENCE: 9
gataagttct agtatatata accctaatta atagtaccaa tattaaatac tatagttaca    60
ccccagggtc ta                                                       72

<210> SEQ ID NO 10
<211> LENGTH: 102
<212> TYPE: DNA
<213> ORGANISM: Clostridium botulinum

<400> SEQUENCE: 10
tagaattgag tttatattta tgtttaccat gataagttct agtatatata accctaatta    60
atagtaccaa tattaaatac tatagttaca ccccagggtc ta                      102

<210> SEQ ID NO 11
<211> LENGTH: 35
<212> TYPE: DNA
<213> ORGANISM: Clostridium botulinum

<400> SEQUENCE: 11
gggaatacat atgtcgacac tccctttac tattt                               35

<210> SEQ ID NO 12
<211> LENGTH: 29
<212> TYPE: DNA
<213> ORGANISM: Clostridium botulinum

<400> SEQUENCE: 12
cggaattcta taaatataa ataattttc                                      29

<210> SEQ ID NO 13
<211> LENGTH: 22
<212> TYPE: DNA
<213> ORGANISM: Clostridium botulinum

<400> SEQUENCE: 13
caaattaagt tcatatgtag ac                                            22

<210> SEQ ID NO 14
<211> LENGTH: 20
<212> TYPE: DNA
<213> ORGANISM: Clostridium botulinum

```
<400> SEQUENCE: 14
ggaatcatat gtatatttag                                               20

<210> SEQ ID NO 15
<211> LENGTH: 22
<212> TYPE: DNA
<213> ORGANISM: Clostridium botulinum

<400> SEQUENCE: 15
ctatagtatt taatattggt ac                                            22

<210> SEQ ID NO 16
<211> LENGTH: 19
<212> TYPE: DNA
<213> ORGANISM: Clostridium botulinum

<400> SEQUENCE: 16
gagcataaat agaattgag                                                19
```

PRODUCTION OF ACID AND SOLVENT IN MICROORGANISMS

CROSS-REFERENCE TO RELATED APPLICATIONS

This application is a 371 U.S. National Stage of International Application No. PCT/EP2009/008961, filed Dec. 15, 2009. This application claims priority to German Patent Application No. 10 2009 064 249.5, filed Dec. 20, 2008. The disclosures of the above applications are entirely incorporated by reference herein.

The invention relates to a method and means for bioengineered, fermentative production of solvents, in particular butanol, acetone and ethanol, as well as short-chained carboxylic acids such as acetic acid and butyric acid, particularly in host cells of the species *Clostridium*. The invention provides new methods and means for the regulation and expression of enzyme activities of the host cell that are involved in acid production and/or solvent production.

PRIOR ART

Some strains of the species *Clostridium*, in particular, *Clostridium acetobutylicum* are able to form solvents, primarily butanol, acetone and ethanol from carbon sources such as carbohydrates, for example monosaccharides, disaccharides, starch and other polysaccharides. Bioengineered solvent production from clostridia has been known as the ABE method since the 1920s (U.S. Pat. No. 1,315,585, Weizmann et al.). Beginning with the 1950s, this method became, however, uninteresting because of advances in petro chemistry. In an environment of rising crude oil prices and demands for renewable energy and raw material sources, fermentative methods for synthesizing energy carriers and raw materials have again become attractive for economic as well as ecological reasons.

In prior art, discontinuous (batch-wise) as well as continuous fermentation methods are known. The butanol yields of the fermentation of carbohydrates using clostridia are still too low in known methods to be economically attractive. To increase the yield and the volumetric productivity, mutants and genetically modified clostridia have been developed in the meantime. Sometimes, different clostridia populations are co-cultivated. Even continuous fermentation has been developed further. In spite of that it has been shown that the increases that can be achieved with these means are still too small. Moreover, genetically modified organisms have special requirements during cultivation and are unstable, which makes the bioengineering method more difficult and expensive. It is therefore desirable to further improve the yield capacity of solvent production in microorganisms, in particular of the species *Clostridium*.

An uncontrollable increase of solvent production is not desired. In co-cultures that are used to expand the substrate spectrum or to increase yield, solvent-sensitive organisms can also be present so that targeted control and regulation of the solvent production/solvent concentration in the culture medium becomes necessary.

Butyric acid is an important raw material for producing butyric acid esters that are, for example, used as scent and flavoring agents, of cellulose butyrate, a weather-proof and impact-resistant plastic, as well as in pest control agents. Moreover, butyric acid and butyrate are also significant as prophylactics and in therapy of the human and animal body. Production of butyrate (and also acetate) as metabolite of probiotic intestinal bacteria, contributes to the maintenance and recovery of intestinal epithelia) function. Externally supplied butyrate has been used since recently for the prophylaxis and therapy of infectious intestinal diseases. Low concentrations of butyrate in the large intestine can, in contrast, cause diseases and initiate, for example, the differentiation of cancer cells in the colon. Microorganisms that form optional short-chained carboxylic acts such as butyrate, in particular bacteria of the species *clostridium* occur naturally in the intestine, in particular in those of monogastric animals and humans. It is desirable to use organisms, in particular clostridia, as probiotic organisms in order to maintain the health of the intestine and in particular, to make therapy possible for chronic inflammable intestinal diseases, diarrhea, irritable bowel syndrome and constipation.

In addition to solvent production, such microorganisms are also considered for the bioengineered production of short-chained carboxylic acids, in particular butyric acid and acetic acid, and especially on a large scale.

While butyric acid has been synthesized using the classic, chemical methods up to now, as a rule, using catalytic oxidation of butanol or also by oxo synthesis from propene and carbon monoxide, the bioengineered production of butyric acid occurs primarily through direct fermentation of C2-C6 bodies, primarily of carbohydrates such as glucose or splitting products such as glycerol. Advantageously, the bioengineered synthesis does not require any petrochemical starting compounds such as propene, so that production is possible from renewable resources, which is independent of petrochemical methods.

However, the known bioengineering methods for producing butyric acid from carbohydrates are in need of improvement. In particular, microorganisms used up to now as organisms that produce solvents are, as is known, not primary and easily usable for synthesizing short-chained carboxylic acids, in particular by butyric acid. The yield of short-chained carboxylic acids is too low using such organisms. Therefore, there is also the need to be able to better regulate and especially stimulate and increase the synthesis of short-chained carboxylic acids, in particular butyric acid, in such cells.

OBJECTIVE OF THE INVENTION

The invention is primarily based on the technical problem of providing methods and means for its execution, as a result of which solvents, especially butanol and perhaps acetone and ethanol, or alternatively short-chained carboxylic acids, especially butyric acid/butyrate and perhaps acetic acid/acetate can be produced by bioengineering in a microbiological host cell, in particular in a solvent-forming host cell of the species *Clostridium* with high yield and primarily at high volumetric productivity. Thereby, the technical problem also consists of providing improved means for regulation, in particular for the increase of solvent production and alternatively, for increasing the production of short-chained carboxylic acids in these host cells. Thereby, these means are to be usable more easily and more reliably and also in various species of the host cell species and in particular, for an increase in yield and preferably also lead to volumetric productivity in the fermentation.

A technical problem that is connected with this is the provision of means that make an especially easy and effective control of the metabolic activities and in particular, enzyme activities possible in the host cell within the context of the solvent production, and perhaps carboxylic acid production.

SUMMARY OF THE INVENTION

The underlying technical problem is primarily solved by providing a nucleic acid molecule that is a regulator of the solvent production or is directly connected with such a regulator. The regulator modulates or regulates, i.e. induces, stimulates or suppresses the expression of at least one gene, which codes at least one metabolic factor, especially the enzyme activity of the solvent production in a host cell. A solvent-producing host cell is preferably selected from the species *Clostridium*.

In a first aspect, the invention concerns a nucleic acid molecule suitable for modulating the expression of at least one enzyme activity of the solvent and/or acid production of a host cell, whereby the molecule has a nucleic acid sequence that is selected from:
    a) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10,
    b) complementary sequences thereof, and
    c) modified sequences and fragments with sequences according to (a) or (b) that have at least 80% sequence congruence and code the function of a regulator for modulating the expression of this enzyme activity.

Preferably, the nucleic acid molecule is an RNA molecule. Preferably, the modulation of the enzyme activity occurs by means of the regulation of at least one process, selected from:
    transcription of preferably at least one gene that codes the enzyme activity, and
    translation of at least one gene transcript into a polyamino acid molecule that has or mediates the enzyme activity,
    whereby the nucleic acid molecule attaches to at least one structure that is mediating this process and modulates its function.

In a second aspect, the invention concerns a nucleic acid molecule that is a genetic mutant of a nucleic acid molecule characterized according to the first aspect, whereby the at least one genetic mutation is preferably selected from the inversion, deletion and insertion of at least one nucleotide.

In a third aspect, the invention concerns a genetically modified host cell with modified acid and/or solvent production in which the expression of the nucleic acid molecule according to one of the preceding aspects, in particular according to the first aspect, is inhibited or prevented. Preferably, this cell is a knock-out mutant of the solB gene and/or a homolog or ortholog of such.

In a fourth aspect, the invention concerns a genetically modified host cell with modified acid and/or solvent production which contains the nucleic acid molecule according to one of the preceding aspects, in particular according to the first aspect, as heterologous gene, preferably one or several copies of such.

In a fifth aspect, the invention concerns a vector containing at least one expressible copy of the nucleic acid molecule characterized in the preceding aspects. Preferably, the nucleic acid molecule is located expressible in sense orientation. In an alternative variant, the nucleic acid molecule is located expressible in antisense orientation.

In a sixth aspect, the invention concerns a genetically modified host cell with modified acid or solvent production, which contains at least one expressible copy of the nucleic acid molecule characterized in the preceding aspects and/or the vector according to the fifth aspect of the invention, preferably one or several copies of such.

In a seventh aspect, the invention concerns an RNA molecule that is preferably produced or synthesized outside of the cell for modulating the expression of at least one enzyme activity of the acid and/or solvent production in a host cell, whereby the molecule is selected from:
    a) an RNA molecule that is transcribable from the nucleic acid molecule according to one of the preceding aspects, in particular according to the first aspect, and
    b) fragments of (a), having the function of a regulator for modulating the expression of this enzyme activity in the host cell.

In an eights aspect, the invention concerns a host cell with modified acid and/or solvent production in which an RNA molecule is planted according to the sixths aspect of the invention. Preferably the planted RNA molecule is present in sense orientation. In an alternate embodiment, the planted RNA is present in antisense orientation.

In a ninth aspect, the invention concerns a method for producing a genetically modified host cell with modified acid and/or solvent production including the step: genetic modification of the host cell with at least one structure selected from: nucleic acid molecules and vectors according to one of the preceding aspects; in preferred embodiments according to the first aspect, alternatively according to the second aspect and alternatively, according to the third aspect.

Preferably, the host cell is or will be genetically modified so that the nucleic acid molecule is expressed according to one of the preceding aspects, in particular, in sense orientation according to the first aspect of the invention. In an alternative variant, the host cell is or will be genetically modified so that the nucleic acid molecule is expressed according to one of the preceding aspects, in particular according to the first aspect of the invention, in antisense orientation.

In a tenth aspect, the invention concerns a method for producing a genetically modified host cell with modified acid and/or solvent production, containing the step: planting of the RNA molecule according to one of the preceding aspects, in particular, according to the first or seventh aspect of the invention.

In an eleventh aspect, the invention concerns a method for the biotechnological production of solvent, preferably selected from acetone, butanol and ethanol, in particular butanol containing the steps:
    Providing a host cell according to the invention, in which the effective concentration of the transcript of the nucleic acid molecule characterized in the first aspect of the invention, is decreased, compared to the wild type of the cell;
    cultivating the host cell in culture medium and in the presence of a substrate under conditions that make the formation of solvent from substrate possible; and
    obtaining the solvent from culture medium and/or the host cell.

In a twelfth aspect, the invention concerns a method for the bioengineered production of short-chained carboxylic acids, in particular butyrate and/or acetate, or butyrate and/or acetic acid containing the steps:
    providing a host cell according to the invention, in which the effective concentration of the transcript of the nucleic acid molecule characterized in the first aspect of the invention, is increased compared to the wild type of the cell;
    cultivating the host cell in a culture medium and in the presence of a substrate subject to conditions that make the formation of short-chained carboxylic acids possible from the substrate; and
    obtaining the short-chained carboxylic acid from culture medium and/or the host cell.

DESCRIPTION OF FIGURES

FIG. 6A), C. acetobutylicum synthetic 3'solB 115 bp antisense (pBS15; FIG. 6B), C. acetobutylicum synthetic 5'solB 72 bp antisense (pBS16; FIG. 6C) and C. acetobutylicum synthetic 5'solB 102 bp antisense (pBS17; FIG. 6D)

DETAILED DESCRIPTION OF THE INVENTION

The invention is characterized in more detail with the aid of the figures and the exemplary embodiments, which are not to be understood as being limiting in any way.

The technical terms used in the context of the description of the invention are understood in the conventional sense as they are known to the person skilled in the art, except where information deviating from such is expressly stated.

The sequence protocol contains:

the sequence of the solB gene with promoter region and terminator region (SEQ ID NO: 1):

```
TTCAGAAGTCTACAAATTAAGTTTATATTTAGACCCTGGGGTGTA

ACTATAGTATTTAATATTGGTACTATTAATTAGGGTTATATATAC

TAGAACTTATCATGGTAAACATAAATATAAACTCAATTCTATTTA

TGCTCCTATAAAATTTTATAATATAGGAAAACTGCTAAATGTAAA

TTATACGTTTACATTTAGCAGTTTATTTT
``` the sequence of the solB gene without promoter region (SEQ ID NO: 2):

```
TAGACCCTGGGGTGTAACTATAGTATTTAATATTGGTACTATTAAT

TAGGGTTATATATACTAGAACTTATCATGGTAAACATAAATATAAA

CTCAATTCTATTTATGCTCCTATAAAATTTTATAATATAGGAAAACT

GCTAAATGTAAATTATACGTTTACATTTAGCAGTTTATTTT
``` the sequence of the solB gene without promoter region and without terminator region (SEQ ID NO: 3):

```
TAGACCCTGGGGTGTAACTATAGTATTTAATATTGGTACTATTAAT

TAGGGTTATATATACTAGAACTTATCATGGTAAACATAAATATAAA

CTCAATTCTATTTATGCTCCTATAAAATTTTATAATATAGGAAAA
```

5'del solB fragment (SEQ ID NO: 4), in plasmid pBS1 for the production of C. acetobutylicum solB sense mutant:

```
TATGTAGACCCTGGGGTGTAACTATAGTATTTAATATTGGTACTAT

TAATTAGGGTTATATATACTAGAACTTATCATGGTAAACATAAATA
```

-continued
TAAACTCAATTCTATTTATGCTCCTATAAAATTTTATAATATAGGAA

AACTGCTAAATGTAAATTATACGTTTACATTTAGCAGTTTATTTTAA

ACCTTCATATTTTTCTAAATATACA solB fragment (SEQ ID NO: 5), in plasmid pBS7 for producing *C. acetobutylicum* synthetic solB sense mutant:

TCCTTAAGATATAGCTTCTTTTATGTAGTATTATTTCAGAAGTCTA

CAAATTAAGTTTATATTTAGACCCTGGGGTGTAACTATAGTATTTA

ATATTGGTACTATTAATTAGGGTTATATATACTAGAACTTATCATG

GTAAACATAAATATAAACTCAATTCTATTTATGCTCCTATAAAATTT

TATAATATAGGAAAACTGCTAAATGTAAATTATACGTTTACATTTA

GCAGTTTATTTTAAACCTTCATG antisense solB fragment (SEQ ID NO: 6), in plasmid pBS13 for producing *C. acetobutylicum* synthetic solB antisense mutant:

TCCTTAAGATATAGCTTCTTTTATGTAGTATTATTTCAGAAGTCTA

CAAATTAAGTTTATATTTTTTCCTATATTATAAAATTTTATAGGAGC

ATAAATAGAATTGAGTTTATATTTATGTTTACCATGATAAGTTCTA

GTATATATAACCCTAATTAATAGTACCAATATTAAATACTATAGTTA

CACCCCAGGGTCTACTGCTAAATGTAAATTATACGTTTACATTTA

GCAGTTTATTTTAAACCTTCATG

3' 75 bp solB fragment (SEQ ID NO: 7), in plasmid pBS14 for producing *C. acetobutylicum* synthetic solB 3' 75 bp mutant:

TTTTCCTATATTATAAAATTTTATAGGAGCATAAATAGAATTGAGTT

TATATTTATGTTTACCATGATAAGTTCT

3' 115 bp solB fragment (SEQ ID NO: 8), in plasmid pBS15 for producing *C. acetobutylicum* synthetic solB 3' 115 bp mutant:

TTTTCCTATATTATAAAATTTTATAGGAGCATAAATAGAATTGAGTT

TATATTTATGTTTACCATGATAAGTTCTAGTATATATAACCCTAATT

AATAGTACCAATATTAAATAC

5' 72 bp solB fragment (SEQ ID NO: 9), in plasmid pBS16 for producing *C. acetobutylicum* synthetic solB 5' 72 bp mutant:

GATAAGTTCTAGTATATATAACCCTAATTAATAGTACCAATATTAA

ATACTATAGTTACACCCCAGGGTCTA

5' 102 bp solB fragment (SEQ ID NO: 10), in plasmid pBS17 for producing *C. acetobutylicum* synthetic solB 5' 102 bp mutant:

TAGAATTGAGTTTATATTTATGTTTACCATGATAAGTTCTAGTATAT

ATAACCCTAATTAATAGTACCAATATTAAATACTATAGTTACACCC

CAGGGTCTA primer according to the following exemplary embodiments (SEQ ID NO: 11 bis SEQ ID NO: 16):

to amplify the ptb-buk promoter (NdeI):

KL08 (SEQ ID NO: 11):
GGGAATACATATGTCGACACTCCCTTTTACTATTT to amplify the ptb-buk promoter (EcoRI):

KL09 (SEQ ID NO: 12):
CGGAATTCTATAAAATATAAATAATTTTC to amplify the promoter-less solB gene (NdeI):

sRNAshort_new_F (SEQ ID NO: 13):
CAAATTAAGTTCATATGTAGAC to amplify the promoter-less solB gene (NdeI):

sRNA_new_R (SEQ ID NO: 14):
GGAATCATATGTATATTTAG forward-primer for RT PCR:

snRNA_F (SEQ ID NO: 15):
CTATAGTATTTAATATTGGTAC reverse primer for RT PCR:

snRNA_R (SEQ ID NO: 16):
GAGCATAAATAGAATTGAG

*C. acetobutylicum* is a gram-positive, strictly anaerobic and endospore-forming soil bacterium that has a biphasic fermentation metabolism. Historically, all strains of the species *Clostridium* were described as *Clostridium acetobutylicum*. Molecular genetic analyses showed that *C. acetobutylicum* consists of at least four different species, *C. acetobutylicum, C. beijerinckii, C. saccharobutylicum* and *C. saccharoperbutylacetonicum*, which are also different in the precise structuring of the genome. Primarily sugar-containing substrates (carbon sources) are converted in the first phase of the metabolism that accompanies the logarithmic phase of growth, first into acetic acid (acetate) and butyric acid (butyrate), while in the second phase of the metabolism, now, the solvents acetone and butanol are formed. The changeover of the metabolism from acid production to solvent production regularly occurs in known manner during the transition into a static phase of growth. Acid concentrations that are too high would lead to a breakdown of the proton gradient via the cytoplasm membrane. On account of the changeover of the metabolism to the production of the neutral solvents, the acid titer is reduced.

Moreover, some of the acids of the medium can be absorbed again. The endospore formation is initiated. As the solvents acetone and butanol are formed only at a late point in time of the growth phase, the solvent formation in the organism is rigorously regulated. Regulation of the solvent formation or the regulation of the genes involved in solvent formation thus represents a primary starting point from which solvent production of clostridia can be improved.

In *C. acetobutylicum*, the genes required for solvent formation are localized to at least five separate operons, (sol operon, adc operon and adhE2 operon on a mega plasmid, as well as bdhA operon and bdhB operon on the chromosome).

Figure 1A:
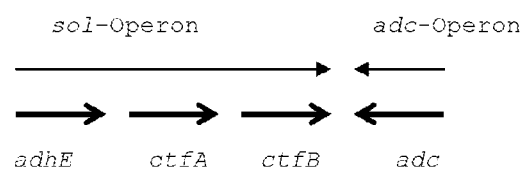
FIGS. 1A, B: Schematic illustrations (not to scale) of the sol operon in *C. acetobutylicum*, FIG. 1A, and in other solvent-forming clostridia, FIG. 1B.
Figure 1B:
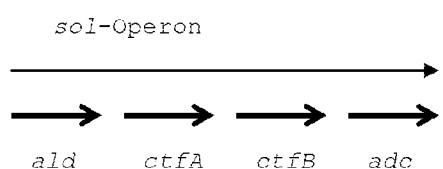

In addition to *C. acetobutylicum*, the strains *C. beijerinckii*, *C. saccharobutylicum* and *C. saccharoperbutylacetonicum* are also capable of solvent production. In these strains, the genes of the sol operon and the adc operon, different than for *C. acetobutylicum*, form a joint polycistronic operon, which is not localized on a mega plasmid, but on the chromosome. This sol operon does not contain any aldehyde/alcohol dehydrogenase (AdhE), but an aldehyde dehydrogenase (Ald). In FIGS. 1A and 1B, the two versions of sol operons of clostridia are shown schematically.

Figure 2:
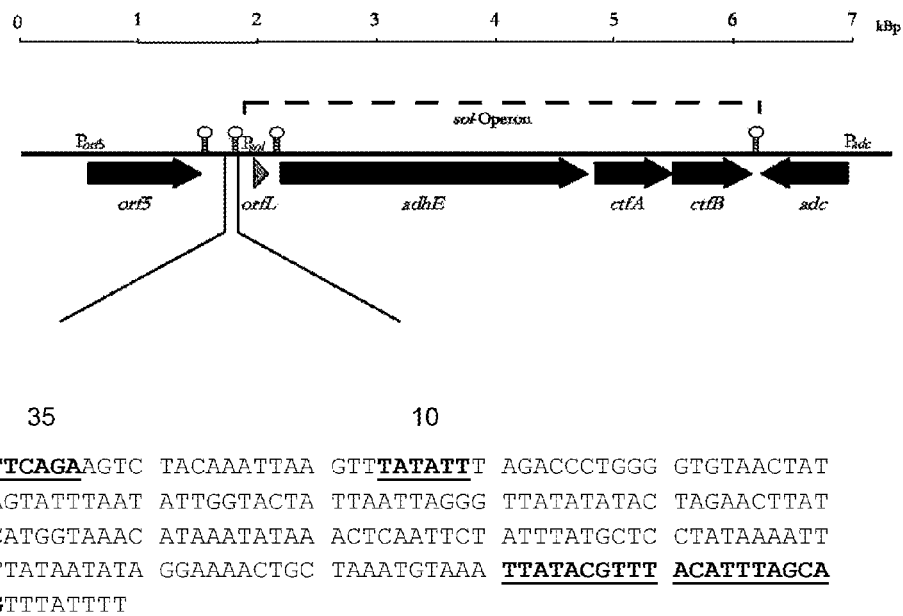
FIG. 2: Position and sequence of the solB gene in the inter-genetic region of the orf5 gene and the sol operon; Legend: orf5: open reading frame; orfL: open reading frame; adhE: aldehyde/alcohol dehydrogenase; ctfA/ctfB: acetocetyl-CoA: acetate/butyrate: CoA-transferase; adc: acetoacetate decarboxylase

Without wanting to be tied to the theory, in *C. acetobutylicum*, most of the genes that are directly or indirectly involved in solvent formation are located separate from the bacteria chromosome (3.9 Mbp) on a mega plasmid pSOL1 the size of 192 kbp. The genes of acetoacetyl-CoA are directly involved in solvent formation:

Acetate/butyrate: CoA-transferase (CoA-transferase, ctfA and ctfB), acetoacetate-decarboxylase (adc), butanol-dehydrogenases A and B (bdhA and bdhB) and aldehyde/alcohol dehydrogenase E (adhE) with the potential membrane-bound electron-transferor OrfL (orfL). The genes orfL, adhE, ctfA and ctfB thereby form the polycistronic sol operon, which is localized divergent with respect to adc operon. (FIG. 1A) The gene for glycosylase/deglykosylase (orf5) is located upstream of the sol operon. FIG. 2 shows a schematic illustration of the sequence region on the mega plasmid pSOL1 that was described.

In the intergene region between the orf5 gene and the sol operon, the solB gene according to the invention is located, which codes a small, uncoded, regulative RNA (sRNA). In FIG. 2, the corresponding sequence region of the intergene region is shown. FIG. 2 highlights the sequence regions of a potential $\sigma^4$-dependent promoter structure with a 35 region (consensus: TTGACA) and a 10 region (consensus: TATAAT) at a distance of 17 bp, and a hair pin structure ($\Delta G=-17.35$ kcal/mol) followed by a poly-U sequence, that perhaps illustrates a rho-independent terminator. The longest open reading frame (ORF) in this region (FIG. 2: position 102 to 146) would code for a protein of 14 amino acids. This ORF and all other ORFs found are not preceded by a conserved ribosome attachment site.

Figure 3:
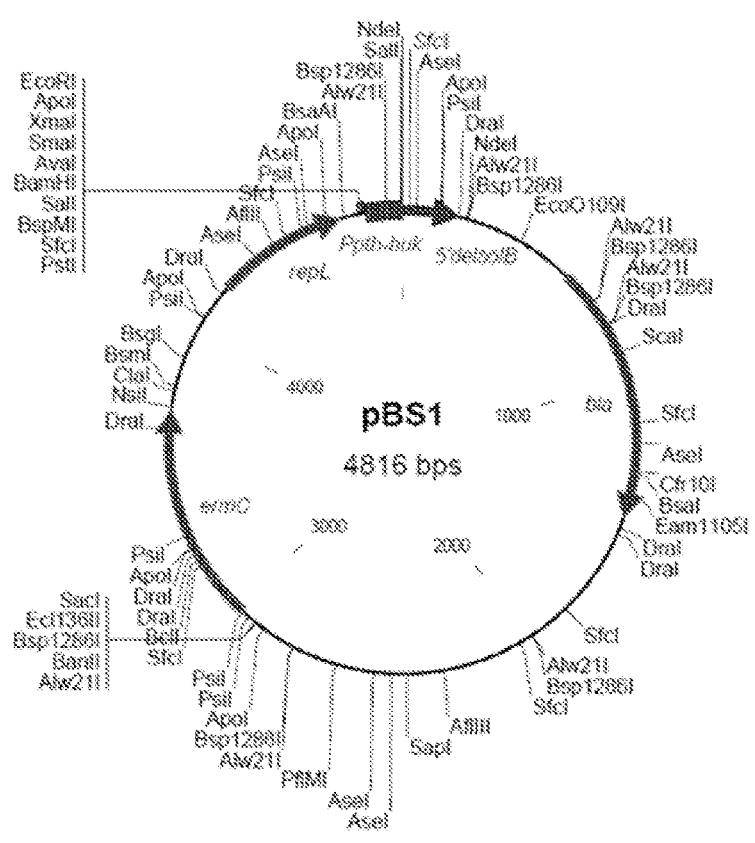
FIG. 3: The plasmid card of vector pBS1 according to the inventing for overexpression of the promoter-less solB gene; cloning of solB without promoter (SEQ ID NO: 2) in sense orientation with ptb/buk promoter on the basis of plasmid pIMP1 for generating a C. acetobutylicum solB sense mutant according to the invention

The potential promoter in the 5' region of the solB gene is active during the entire growth phase of strain *C. acetobutylicum* on phosphate-limited minimal medium, and that specifically in the acid, as well as in the solvent phase. The SolB transcript (SolB-mRNA) can be verified in both phases, i.e. during the entire growth phase (FIG. 3).

Any vector that is capable of replication in *C. acetobutylicum*, for example, a vector on the basis of pIMP1, is preferably provided with a constitutive, preferably ptb-buk promoter (promoter of *C. acetobutylicum* phosphotransbutyrylase-butyratkinase operon), or alternatively preferred, provided with an inducible promoter, preferably luxR analog. Behind the promoter, preferably either the complete, or alternatively preferred a promoter-less sequence of the solB gene can be cloned, in order to obtain the genetically modified host cell according to the invention.

The nucleic acid molecule according to the invention is preferably (a) a DNA molecule, which is or will be transcribed into a regulator, in particular an RNA molecule, or (b) an RNA molecule that functions as a regulator, or engages in reciprocal action with a transcription system, primarily in order to regulate the expression of at least one of the genes that codes for the enzyme activity of acid and/or solvent production.

The nucleic acid molecule according to the invention, or used according to the invention, is characterized primarily thereby, that it has at least one or several of the nucleic acid sequences, or has such exclusively, which are selected from the sequences according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10, complementary sequences thereof, as well as modified sequences and fragments, that together with these have at least an 80%, in particular at least 90% sequence congruence. In a special variant of the invention, the nucleic acid molecule consists of one of these sequences, i.e. it essentially has no other, or preferably no additional nucleotides.

The invention also comprises those nucleic acid molecules that have homologous sequences with respect to it, but which are characterized thereby, that these at least fulfill the function according to the invention of regulation or modulation of the expression of the enzyme activity in the host cell (functional analogs). Homologous sequences within the scope of the invention are primarily those sequences that are obtained by exchange or omission of one or several nucleotides in the sequence. The person skilled in the art knows well-established methods of inversion, deletion, addition and of nucleotide exchange. In preferred variants of the invention—in the nucleic acid molecule with homologous sequence—1 to 10% of the total number of nucleotides in the molecule are replaced, complemented or removed, in particular, these are 1 to 20, preferably 1 to 10 nucleotides in the preceding characteristic sequences.

The invention also comprises functionally analogous nucleic acid molecules that are homologs to the nucleic acid molecules that are characterized herein. The invention also comprises functionally analogous nucleic acid molecules that are orthologs to the nucleic acid molecules characterized herein. In this context, the person skilled in the art knows the possibility of finding genetic homologs and orthologs; hereby, he uses databases and/or known bioinformatics.

The invention also comprises those functionally analogous nucleic acid molecules in which one or more nucleotides is/are replaced by one or more nucleotide analogs, purine derivatives or pyrimidine derivatives.

The invention further also comprises genetically modified or mutated nucleic acid molecules that are derived from such, which are primarily characterized thereby, that their transcription in the host cell is suppressed, or a mutated transcript is obtained, which at least does not fulfill the regulation function according to the invention, or the modulation of expression of enzyme activity in the host cell. In this context, the person skilled in the art knows the possibilities of generating genetic mutations. To produce the mutation at the nucleic acid molecule, in particular the solB gene, the person skilled in the art relies on established methods. These are preferably selected from: insertion, deletion, inversion, substitution and addition of at least one nucleotide. A preferred application of such mutated nucleic acid molecules is providing knock-out mutants of host cells, in particular, providing solB knock-out mutants, and providing knock-out mutants of homologs and/or orthologs of such. The production of mutants is preferably performed in known manner. A preferred method is homologous recombination. But the invention is not limited to this method.

Preferably, a nucleic acid molecule according to the invention is present in expressible form, and preferably in an expression cassette. In it, the nucleic acid molecule can be present once or preferably in multiple copies. Preferably, it lies in the genome of the host cell.

In a preferred variant, it is present in the chromosome. In a different preferred variant, it is present in a plasmid or mega plasmid of the cell. In a preferred variant it is present exclusively, or preferred additionally, in one or several expression vectors that have been planted into the host cell. Preferably, it is present as DNA molecule and is preferably transcribed into one or several RNA molecules.

The nucleic acid molecule according to the invention is a regulator or stands in direct connection with such a regulator that preferably regulates at least one process of the gene expression, selected from transcription and translation of at least one of the metabolically relevant genes for at least one enzyme activity of the acid and/or solvent production, and preferably also increases or preferably inhibits. Preferably, the at least one enzyme activity is coded on at least one gene location of the host cell, in particular a clostridia cell, which is selected from sol operon and adc operon.

The inventors found it surprising that the nucleic acid molecule according to the invention functions primarily as small, uncoded regulatory RNA (SolB transcript). If it is present as DNA in an alternative variant according to the invention, it can be transcribed into such RNA. The RNA molecule according to the invention represents, if it is present in the cell in high concentration, a modulator and preferably a repressor of solvent formation, primarily of butanol formation.

The RNA molecule either performs the effect on the enzyme activity of the host cell alone, or if necessary, in combination with other factors. Preferred factors or co-factors are RNA molecules, DNA molecules and proteins, for example, in the form of co-repressors.

Thus, the invention provides an advantageous use of the "solB gene", which is transcribable into a central regulator molecule (SolB transcript) of the enzymes of the solvent synthesis, in particular of acetone and butanol formation. The invention thus provides the use of the "gene" preferably as DNA molecule, as well as use of its transcript, preferably as RNA molecule, and specifically as the preferred means that makes the regulation of the acid and/or solvent production in the host cell possible.

In addition to the SolB transcript of the SolB wild type, preferably of *C. acetobutylicum*, the invention also comprises its fragments and functional analogs, i.e. also molecules that interact in analogous functionality with the target structures target RNA, or target DNA, or target protein. The invention comprises their use for regulation or modulation of the gene expression in host cells, primarily in solvent-forming clostridia and primarily in connection with the regulation of solvent and acid production in host cells.

The inventors found it surprising that the SolB transcript according to the invention, as well as its analogs according to the invention, derivatives and fragments, work as regulator directly at the RNA level, i.e. they function as RNA molecules. In a preferred embodiment, the molecule according to the invention is itself an RNA, or an RNA analog. Advantageously, it does not need to first be translated into a protein or peptide, as in coded RNAs. It can perform the regulatory effect preferably directly on the target structures as a so-called "small uncoded regulatory RNA".

In a preferred embodiment according to the invention, this RNA provides stimulation of the production of short-chained carboxylic acids, in particular butyric acid, especially in cells of the species *Clostridium*, or in particular, in primary solvent-forming organisms.

In connection with the present invention, "target structures" are primarily understood as being effectors and molecules of the transcription apparatus, as well as those of translation, which are for expression and synthesis of genetically coded enzyme activities.

A functionally analogous nucleic acid molecule (functional analog) within the scope of the invention attaches to at least one of the attachment sites that function regulatory in the genome of the organism, preferably to the regulatory elements of at least one gene that is involved in the acid and/or solvent production. Such an attachment site can itself be an RNA transcript of this gene. Thus, the RNA molecule according to the invention has at least the attachment sequence that is active regulatory in common with the SolB transcript. Subject matter of the invention is thus also a regulatory fragment that has an attachment sequence that is a functional analog according to the invention. This preferably has a sequence of a length of 5 bp or more, or 6 bp or more, or 7 bp or more, of 8 bp or more, 9 bp or more, 10 bp or more, 11 bp or more, 12 bp or more or 15 bp or more, which is homologous with the attachment sequence in the SolB transcript or corresponds to such. This attachment sequence is preferred in the sequences according to the invention revealed herein, or consists of such.

Without wanting to be tied to the theory, the nucleic acid molecule according to the invention interacts with mRNA, or with a DNA strand of a certain target gene, i.e. a gene that codes for the enzyme activity, or parts thereof, of the solvent synthesis or the acid synthesis in the cell. In a different or additional characteristic, the nucleic acid molecule according to the invention interacts with one or more co-factors, in particular in the form of proteins.

The interaction occurs especially in complementary sequence regions of the target gene. The sequence region of the interaction, which has the regulation of the system according to the invention as a consequence, can be very short according to the invention. Without wanting to be tied to the theory, approximately 9 bases (bp), for example, 5 to 14 bases (bp) of the SolB RNA molecule are sufficient for an interaction with the target structure (interaction sequence).

Without wanting to be tied to the theory, the interaction with a target mRNA leads to its degradation and/or to the blockade of the pertaining ribosome attachment site, so that the corresponding gene cannot be translated (further). The interaction sequence can preferably be found at several locations in the genome of the host cell, so that the nucleic acid molecule according to the invention can preferably attach several target structures simultaneously, and can thus preferably act regulative on genes for enzyme activities. Preferably, the nucleic acid molecule of the host cell according to the invention regulates all enzyme activities that are connected with solvent or acid production. The nucleic acid molecule according to the invention thus advantageously allows the regulation of several functionally associated targets.

The interaction with the mRNA of the target gene occurs solely by means of SolB or, analogous of an Hfq-mediated RNA systems, as it is known from *E. coli*, if necessary with one or more helper proteins.

Without wanting to be tied to the theory, the decreased effective concentration of the SolB transcript, i.e. the nucleic acid molecule according to the invention, causes a modified and especially an increased solvent production in the cell. The inventors found it surprising that with the expression, or the stronger expression of the solB gene for increasing the concentration of the SolB transcript in the cell, or with the suppression of the expression for decreasing the concentration of the SolB transcript in the cell, the acid and/or solvent production in the cell can be regulated. An increase of the concentration of the SolB transcript or of a functional analog of such according to the invention, surprisingly leads to a decrease of the solvent synthesis and simultaneously to an increase in acid production. Conversely, a decrease in the concentration of the SolB transcript or the functional analog, leads to an increase of the solvent synthesis and to a decrease in acid production.

In a first embodiment of the invention, means and methods are provided for increasing acid production, and in particular to reduce solvent production in the host cell. To this end, the invention concerns primarily steps for increasing the effective concentration of the SolB transcript or a fragment, derivative or analog of such, which has the regulating effect of the SolB transcript (functional analog), in the host cell. The increase of the effective concentration of the SolB transcript or its functional analog in a cell is achieved by known methods. Especially preferred variants are shown in more detail in the following.

To that end, in a preferred variant, a transformed host cell is provided in which the solB gene and/or one or more analogous constructs or derivatives of such are expressed and especially overexpressed. Preferably, this is achieved by transforming the host cell, preferably by at least one expression vector that contains at least one or preferably several copies of a nucleic acid molecule according to the invention, a functional derivative, analog or fragment thereof and specifically preferred, in sense orientation.

The expression of the nucleic acid molecule according to the invention in the host cell is preferably controlled by at least one constitutive promoter, particularly a promoter that can mediate its overexpression. In a preferred variant, the promoter is the original promoter of the solB gene from *C. acetobutylicum* or a homologous promoter. In a different preferred variant, the promoter is the constitutive btb-buk promoter, i.e. the promoter of the phosphotransbutyrylase-butyratkinase operon of *C. acetobutylicum* or a functionally analogous promoter.

Other known methods for overexpression can also be used and are included in the subject matter of the invention. These include, for example, methods for the direct modification of the promoter, in particular the so-called "promoter-up" method, in which primarily the endogenous solB promoter is replaced or complemented by a stronger, particularly a constitutive endogenous promoter ("superpromoter") in a known manner or is mutated, so that it mediates a stronger expression (overexpression) of the solB gene.

In a preferred variant, a sense construct is directly inserted into the cell as DNA or RNA molecule. This is accomplished, for example, by temporary disintegration of the cell membranes by means of electroporation, or by bombardment of the cell ("gene gun"). Sufficient alternative methods are known to the person skilled in the art.

To transform the host cell, preferably one or more plasmids are used, which contain one or more copies of the expression cassette according to the invention and/or one or more copies of the nucleic acid molecule according to the invention.

Figure 4:
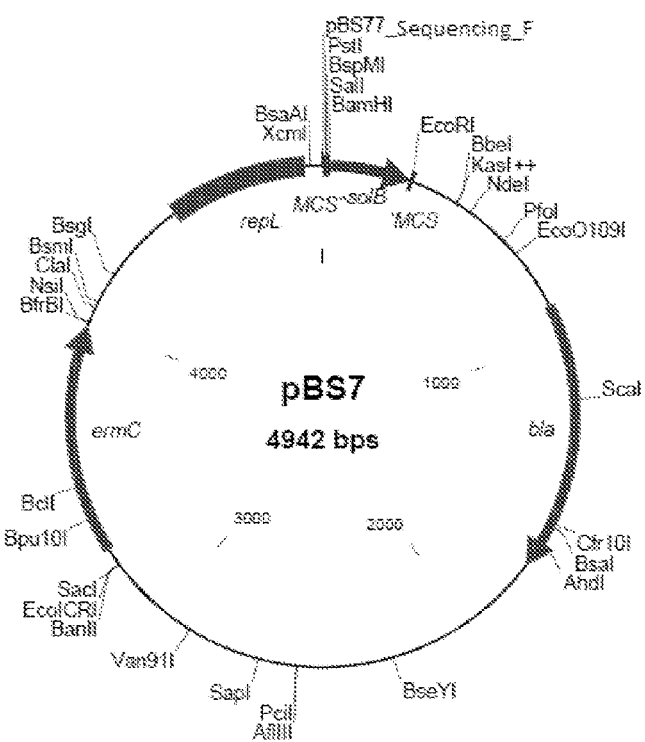
FIG. 4: Plasmid card of vector pBS7 according to the invention for overexpression of the complete solB gene (SEQ ID NO: 1); cloning of solB with solB's own promoter on the basis of plasmid pIMP1 for generating C. acetobutylicum synthetic solB sense mutant according to the invention

Accordingly, a vector which contains the solB gene, i.e. at least one nucleic acid molecule according to the invention or its analog, fragment or a derivative thereof, is also subject matter of the invention, and that, specifically preferred in its sense orientation. Preferably, one or more copies of the nucleic acid molecule are present in expressible form, preferably in at least one expression cassette, particularly preferred in connection with a constitutive or inducible promoter. In a preferred variant, the vector is construed on the basis of the pIMP1 vector. Vector cards of preferably used vectors are shown in FIGS. 3 and 4.

A method for the production of a genetically modified host cell with reduced solvent production and in particular increased acid production is also subject matter of the invention. It includes the steps:
providing a host cell of the species *Clostridium*, and
transforming the host cell with a nucleic acid molecule according to the invention and/or vector that contains one or more nucleic acid molecules according to the invention, preferably in sense orientation,
so that the solB gene or a functional analog, fragment or derivative thereof is overexpressed, or the regulator molecule according to the invention is increasingly synthesized in the host cell, so that the effective concentration of the regulator molecule, in particular the SolB transcript is increases.

Also subject of the invention is a genetically modified cell which exhibits the modified acid and or solvent metabolism according to the means and methods of the invention. In particular, this is a genetically modified host cell, which preferably contains at least one vector according to the invention and/or a nucleic acid molecule according to the invention in sense orientation, preferably exclusively as heterologous gene and in expressible form.

In a particular embodiment of the invention, a nucleic acid molecule according to the invention, particularly the SolB transcript or its functional analogs are produced, preferably directly, outside of a biological organism, primarily by chemical synthesis. The chemical synthesis of the nucleic acid molecule, particularly the RNA molecule, occurs in known manner. The invention thus also concerns methods for the chemical synthesis of the SolB transcript according to the invention that is used, or a functional analog of such. Thereby, the chemical synthesis preferably relies on the sequences according to the inventing that are disclosed herein.

In addition to the chemical synthesis of RNA molecules according to the invention, the invention also concerns the chemical synthesis of desoxy-ribo nucleic acid molecules, i.e. primarily DNA molecules that are transcribable into an RNA molecule according to the invention.

Subject matter of the invention is also the nucleic acid molecule, particularly the RNA molecule for modifying the expression of at least one enzyme activity in a host cell, whereby the molecule is selected from:
a) RNA molecules, which are coded by the nucleic acid molecule according to the invention, preferably selected from: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10, and preferably have its nucleotide sequence, and
b) modifications of fragments thereof that have at least the function of a regulator for modulating the expression of this enzyme activity in the host cell.

An RNA molecule according to the invention or a population still containing at least one second or additional variants of the molecule can be inserted into the host cell in known manner, preferably by attaching an electric field (electroporation) by means of which the cell membranes of the living cells are temporarily made permeable for these small molecules without causing a complete disintegration of the cells.

In this alternative embodiment of the invention, a transformation of the host cells, for example with vectors, is not necessary. The regulation by the at least one RNA molecule that was introduced from outside having the function or the attachment activity of the SolB transcript according to the invention, can take place directly. Advantageously, in this embodiment there is also no dependence on promoters, as in overexpression plasmids.

Further, subject matter of the invention is also a method for increasing acid production, in particular the synthesis of short-chained carboxylic acids, in particular, also acetate and/or butyrate in a host cell, as well as improved methods for their biotechnical production. According to the invention, most of the time, a host cell, especially of the species *Clostridium* is provided, and at least one RNA molecule with the function or attachment activity of the SolB transcript according to the invention is planted into the host cell. For the bioengineered production of these carboxylic acids, the thus modified host cell is cultivated, preferably in the presence of a metabolizable substrate and that specifically under conditions that make the formation of carboxylic acid from the substrate possible. The person skilled in the art knows the possibilities of selecting and finding corresponding conditions that permit the realization of this teaching according to the invention.

In a second embodiment of the invention, means and methods for increasing solvent production in the host cell are provided. The reduction of the effective concentration of the SolB transcript or a functional analog of it in the host cell is, according to the invention, achieved by known methods. Especially preferred variants are explained in further detail in the following.

In a preferred variant it is provided that a solB knock-out mutant of a host cell, particularly of a solvent-forming cell of the species *Clostridium* is provided. Such a solB knock-out is created using known methods, in particular by homologous recombination. Preferably, the invention provides one or several known steps preferably selected from deletion, substitution, insertion and inversion, in particular point mutation of the solB gene or its homolog or ortholog, or other functional analogs in the host cell.

An alternative embodiment is the antisense inhibition of solB gene, its homolog or ortholog or other functional analogs in the host cell. In a preferred embodiment of the invention, the effective concentration of the SolB transcript in the cell is decreased thereby, that preferably by transformation, one or more antisense constructs, preferably in the form of one or several expression vectors, are introduced into the cell. For transforming the host cell, preferably one or several plasmids are used, which contain one or more copies of the antisense construct, preferably in one or more expression cassettes according to the invention.

In a preferred variant, the antisense construct is introduced as DNA or as RNA molecule directly into the cell in known manner. This occurs, for example, by temporary disintegration of the cell membrane by means of electroporation or by bombardment of the cell (gene gun). The person skilled in the art is sufficiently familiar with alternative methods.

Accordingly, the invention also concerns nucleic acid molecules that represent an antisense construct of an endogenous solB gene, its homolog or ortholog, or other functional analogs or a fragment of such. Such nucleic acid molecules according to the invention are derived by inversion of the previously described nucleic acid molecules in known manner. It is understood that the invention concerns all analogs, fragments or derivatives thereof that make the antisense inhibition of the solB gene in the host cell possible according to the invention. The person skilled in the art can easily make such fragments available.

Especially preferred according to the invention are the following fragments of the solB gene: 3'-solB 75 bp (SEQ ID No: 7), 3'-solB 115 bp (SEQ ID No: 8), 5'-solB 72 bp (SEQ ID No: 9), 5'-solB 102 bp (SEQ ID No: 10). Preferred are fragments of the solB gene that are cloned in antisense orientation in an expression vector, and thereby the host cell, preferably a solvent-forming *Clostridium* cell, is transformed.

Figure 5:
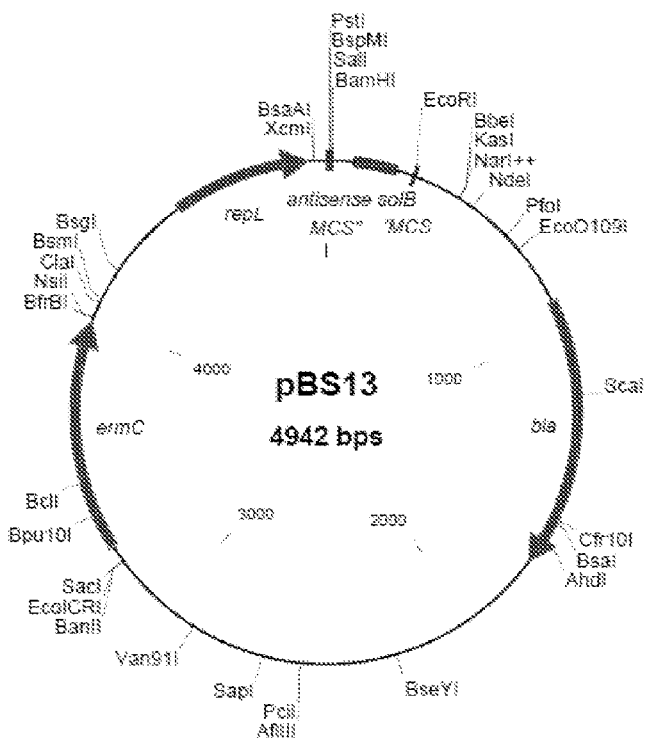
FIG. 5: Plasmid card of vector pBS13 according to the invention for the expression of an antisense construct of the solB gene; cloning of solB antisense orientation with solB's own promoter and terminator (both in sense orientation) on the basis of plasmid pIMP1 for generating a C. acetobutylicum synthetic solB antisense mutant according to the invention
Figure 6A:
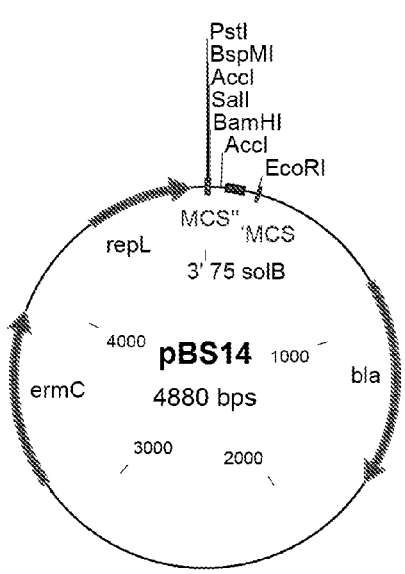
FIGS. 6A-D: Plasmid cards of vectors pBS14, pBS15, pBS16 and pBS17 according to the invention for expressing antisense constructs of fragments (3'solB 75 bp, 3'solB 115 bp, 5'solB 72 bp, 5'solB 102 bp) of the solB gene; cloning of fragments of solB in antisense orientation with solB's own promoter (in sense orientation) and terminator (in sense orientation) on the basis of plasmid pIMP1 for generating mutants according to the invention: C. acetobutylicum synthetic 3'solB 75 bp antisense (pBS14.
Figure 6B:
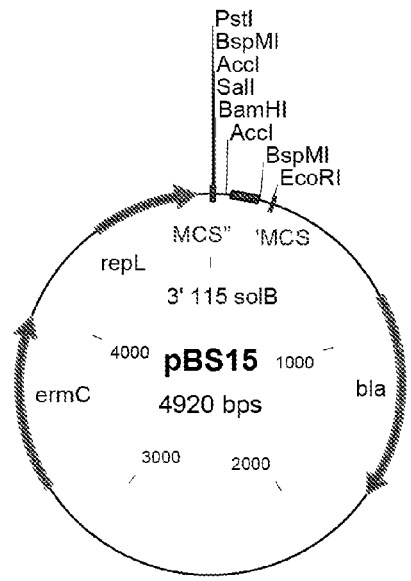
Figure 6C:
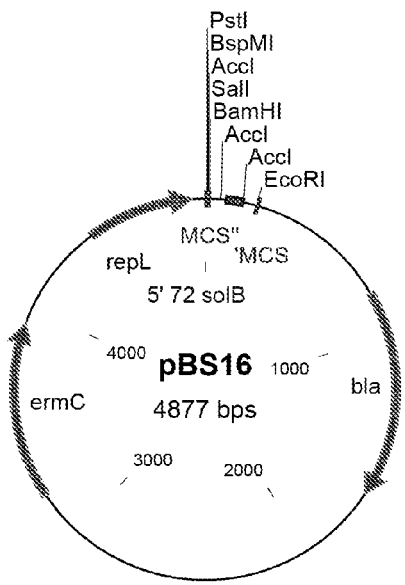
Figure 6D:
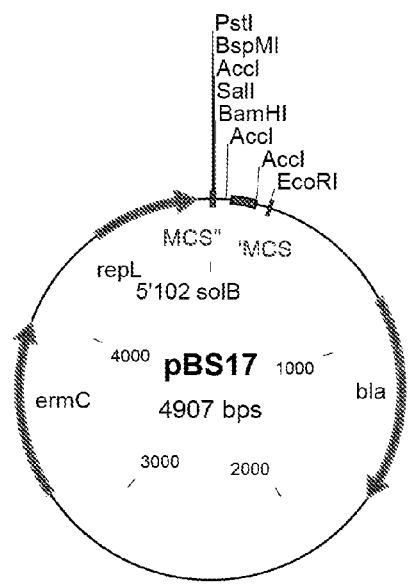

Accordingly, a vector for suppressing the expression of the solB gene in the cell is also subject matter of the invention. It contains a solB gene construct, i.e. at least one nucleic acid molecule according to the invention or its analog, fragment or a derivative of such, and specifically preferred, in antisense orientation. Preferably, one or more copies of the nucleic acid molecule is present in antisense orientation in expressible form, preferably in at least one expression cassette, particularly preferred in connection with a constitutive or inducible promoter. In a preferred variant, the vector is designed on the basis of the pIMP1 vector. Vector cards of preferably used vectors are shown in FIGS. 5 and 6.

Subject matter of the invention is also a method for the production of a genetically modified host cell with modified, especially with increased solvent production, containing the steps:

Providing a host cell, in particular of the species *Clostridium*, and
planting a nucleic acid molecule according to the invention or a vector containing at least one modified solB gene construct, i.e. a nucleic acid molecule according to the invention or its analog, fragment or a derivative of such, and that specifically preferred, in antisense orientation into the host cell, so that the expression of the solB gene or a functional homolog or ortholog of such is suppressed, or the regulator molecule according to the invention, i.e. particularly the SolB transcript is synthesized in the host cell at a reduced level, so that the effective concentration of the regulator molecule is reduced.

Subject matter of the invention is also a host cell which has a modified acid or solvent metabolism with the means and methods according to the invention. In particular, this is a genetically modified host cell, which preferably contains at least one vector according to the invention and/or a nucleic acid molecule in antisense orientation according to the invention, preferably exclusively as heterologous gene and in expressible form.

The invention also concerns a method for increasing solvent production, in particular butanol production in a host cell and improved methods for the bioengineered production of solvents, in particular butanol, whereby at least one host cell modified in this way is provided, in particular of the species *Clostridium*.

The invention also concerns methods for the bioengineered production of solvents, in particular acetone and/or butanol production. To do so, the host cell modified according to the invention, is cultivated preferably in the presence of a metabolizable substrate, and that specifically, preferably under conditions, which make the formation of solvents, in particular of acetone and/or butanol possible out of substrate. The person skilled in the art is aware of the possibilities and of finding and selecting corresponding conditions that permit the realization of this teaching according to the invention.

Subject matter of the invention is also a method for the production of a host cell with modified, in particular with increased solvent production containing the steps:

Providing a host cell, in particular of the species *Clostridium*, and
planting the nucleic acid molecule according to the invention in the form of a, preferably externally synthesized, in particular isolated RNA molecule, and specifically, in antisense orientation, into the host cell, so that the solB gene and/or its functional analog, homolog or ortholog is suppressed or the effective concentration of the transcript is reduced.

In both embodiments of the invention that are characterized above, the host cell modified according to the invention to which reference is made there, in particular, genetically modified, is preferably selected from organisms of the species *Clostridium*, in particular the solvent-forming species, especially preferred from *C. beijerinckii, C. saccharobutylicum, C. saccharoperbutylacetonicum* and *C. acetobutylicum*. The invention is not limited to these cells. The invention can also be applied to, for example, acid and/or solvent-forming genetically modified host cells that have the enzymes for acid and/or solvent production, in particular also homologous or orthologous genes with respect to the solvent-forming clostridia.

The cultivation of the acid and/or solvent-forming host cell provided according to the invention can occur in co-cultivation with other cells of the same species that have a metabolic exchange with the host cells modified according to the invention. For co-cultivation, even other organisms of a different species can be used in order to increase the substrate spectrum. The person skilled in the art is aware of the possibilities of co-cultivation.

The substrate for the synthesis of acid and/or solvents according to the invention is preferably a carbon-containing substrate. It is preferably a vegetable material which preferably has a high content of carbohydrates, primarily starch, lignocellulose, cellulose and/or sugar, as well as fiber material obtained from such, extracts obtained from such, molasses obtained from such, pulps obtained from such and/or juice obtained from such. A preferred vegetable material is corn and/or products derived from it. An additional preferred vegetable material is the sugar beet and/or products derived from it. An additional preferred vegetable material is sugar cane and/or products derived from it, cane trash, etc. Additional preferred materials are grains or fibrous plants and/or products derived from them, straw, stover (grain harvest residuals), especially corn, stover (corn harvest residuals). Preferred grains are rice, wheat, barley, rye, and oats. Preferred starches or sugar sources are horse chestnut, potato, batata, artichoke, cassaya, chicory and soya. Preferred lignocellulose and cellulose sources are nutshells, wood, in particular soft wood, as well as fiber material obtained from such and wood waste, fruit peels and pressed out fruit such as grapes and citrus fruits, grain straw, corn straw and cane trash. In the case of primarily cellulose-containing plants and/or fibrous plants, co-cultures containing primarily cellulose-metabolizing organisms can be used.

Finally, the invention also concerns attachment complexes which are connected with the regulation of the solvent and acid production in the host cell, consisting of or containing at least one nucleic acid molecule according to the invention or its functionally analogous fragment, derivative or analog, with at least one target structure containing the attachment site.

Attachment complexes according to the invention are preferably obtained by methods that include at least the steps:
Providing the nucleic acid molecule according to the invention, which is preferably an RNA molecule, and bringing the nucleic acid molecule in contact with at least one structure that has an attachment site for attaching the nucleic acid molecule, in particular a DNA molecule, RNA molecule and/or protein.

As attachment site, the structure preferably has a homologous base sequence with a complementary sequence that is homologous with the nucleic acid molecule according to the invention, or a homologous sequence region thereof.

Also subject matter of the invention is a kit (kit of parts), in which at least one of the molecules or constructs described herein, in particular in isolated form is contained, or preferably consists of such for the modulation of acid and/or solvent production in a host cell that is characterized herein in further detail.

Subject matter of the invention is also a kit (kit of parts), in which at least one of the genetically modified host cells described herein, in which the effective concentrating of the SolB transcript or a functionally analogous derivative or fragment thereof is increased compared to the wild type of the cell is contained, or preferably consists of it, for the bioengineered production of short-chained carboxylic acid.

Subject matter of the invention is also a kit (kit of parts), in which at least one of the genetically modified host cells described herein, in which the effective concentration of the SolB transcript or a functionally analogous derivative or fragment thereof compared to the wild type of the cell is reduced, contained, or preferably consists of it, for the bioengineered production of solvents.

The invention also concerns the use of the molecules or constructs or kits for modulating the acid and/or solvent production described herein in a host cell that is characterized further. Preferred is the use for increasing the solvent synthesis. Particularly preferred is the use for the synthesis of acetone. Particularly preferred is the use for the synthesis of butanol.

In alternative variants of the invention, the use for increasing the acid synthesis is preferred. Especially preferred is the use for the synthesis of acetate or acetic acid. Particularly preferred is the use for the synthesis of butyrate or butyric acid.

Example 1

Analysis of the solB Expression in *C. acetobutylicum*

1.1 Isolation of Total RNA

After centrifugation (14,000 rpm, 4° C., 1 min), the cells were quickly shock-frozen in 2 ml reaction vessels in liquid nitrogen. The cell sediment was resuspended in 0.7 ml ice-cold ASE buffer (see below) and immediately, 0.7 ml Aqua-Phenol™ heated to 60° C. (water-saturated phenol; from QBiogene) was added and vigorously mixed for 30 seconds. Subsequently, the mixture was incubated for 10 minutes at 60° C. By repeated mixing, the phases were kept in suspension. After centrifugation (13,000 rpm, 10 min, 4° C.), the watery phase was transferred to a 2 ml reaction vessel and mixed with 0.6 ml AquaPhenol™. After mixing, it was again centrifuged and the phenol treatment was repeated until no interphase could be detected any more. Subsequently, an extraction was performed respectively with AquaPhenol™/ReadyRead™ (from QBiogene) (1:1 v/v) or Ready/Red™ (from QBiogene). After completing the treatment, the RNA was subjected to an ethanol precipitation.

ASE Buffer:

| Na acetate | 164 mg | 20 mmol/l |
| SDS | 0.5 g | 0.5% (w/v) |
| EDTA | 37 mg | 1 mmol/l |
| H₂O ad 100 ml | pH 5.5 | |

1.2 Ethanol Precipitation

Precipitation of RNA or DNA was achieved by adding 2.5 vol. ice-cold ethanol (96% v/v) and incubation for at least 30 minutes at −20° C. After centrifugation (14,000 rpm, 30 minutes, 4° C.) the sediment was washed with 1 ml ethanol (70%, v/v) and centrifuged again. After that, the sediment was dried in a SpeedVac vacuum centrifuge. Depending on the density of the initially used culture, the sediment was dissolved in 20-50 µl DEPC water (diethyl pyrocarbonate). The RNA prepared in this way was still often contaminated with DNA, so that a DNase treatment could follow.

1.3 DNase Treatment of Watery RNA Solutions

For the DNase treatment, RNase-free DNase ("deoxyribonuclease I, RNase-free, from Fermentas) was used as a starter with a total volume of 200 µl, which contained 20 µl 10× DNase buffer (10× reaction buffer with $MgCl_2$, from Fermentas GmbH) and 50 U DNase I. After an incubation of 1 hour at 37° C., 20 µl Na acetate solution (3 mol/l, pH 5.2) was added, and a phenol/chloroform extraction and an ethanol precipitation was performed.

To order to obtain RNA that was completely free of DNA, this treatment could be repeated one or twice. A standard PCR on RNA served as control for DNA contamination. In the case of completely digested DNA, no specific PCR product was detectable in the EtBr-colored agarose gel.

The RNA was stored in 20-50 µl DEPC water at −70° C.

1.4 Phenol/Chloroform Extraction

To free DNA and/or RNA solutions from protein contaminations, the DNA or RNA solution was added to 1 vol. phenol/chloroform/isoamyl alcohol (25:24:1, v/v/v), mixed for 30 seconds and centrifuged for phase separation (13,000 rpm, 5 minutes, RT). The upper watery phase was subsequently transferred to a new reaction vessel and the procedure was repeated as many times as necessary so that after centrifugation, no protein phase was detected any more. Thereupon, for the removal of potentially present phenol residues—in a new reaction vessel—1 vol. chloroform/isoamyl alcohol (24:1, v/v) was added to the upper phase, mixed for 30 seconds and centrifuged again. Finally, the upper, DNA-containing phase was precipitated with ethanol.

1.5 RT PCR

The RT PCR was used to rewrite the RNA into single-strand cDNA with the help of the enzyme, reverse transcriptase. Based on this cDNA, in a second step, which corresponds to a standard PCR, a specific product was amplified. An amplificat was obtained only if the corresponding mRNA of a gene, or an operon had been formed during the course of the transcription.

For the SolB transcript, per RT PCR experiment, approximately 500 ng total RNA was used as template strand. As primer, snRNA_R (reverse primer) was used for the cDNA synthesis and the subsequent PCR was complemented with primer snRNA_F (forward primer). In the negative controls, the reverse transcriptase was replaced with water. For each RT PCR experiment, the starting materials were: RNA: 0.01-0.5 µg; reverse primer (20 µmmol/l): 1.5 µl (2.7 µmol/l); RNase-free water: ad 11 µl. The starting materials were incubated for 5 minutes at 70° C. and subsequently quickly cooled to 4° C. After adding RT reaction buffer (5×): 4 µl (1×), dNTP mixture (10 mmol/l): 2 µl (1 mmol/l); Ri-bolock™ (from Fermentas) (40 U/µl): 1 µl (40 U); M-MuLV reverse transcriptase (from Fermentas) (20 U/µl): 2 µl (40 U), the probes were incubated for 1 hour at 37° C. Reverse transcriptase was replaced with 2 µl water for the negative control.

After inactivation for 10 minutes at 70° C., a standard PCR with taq DNA polymerase followed. The following were used for each experiment: taq polymerase (1 U/µl) 5 µl (5 U); $(NH_4)_2SO_4$ reaction buffer (10×): 5 µl (1×); forward primer (20 µmol/l): 1.5 µl (0.6 µmmol/l); $H_2O$: ad 50 µl. The DNA fragments were separated and analyzed in a non-denaturing agarose gel electrophoreses.

1.6 Standard PCR

The standard PCR for verifying plasmid was done with taq DNA polymerase (from Fermentas GmbH). To amplify DNA regions that were subsequently cloned, the polymerase "PowerScript DNA polymerase short" (from PAN-Biotech) or "High Fidelity PCR Enzyme Mix" (from Fermentas) was used.

A typical PCR experiment had the following components: reaction buffer (10×): 5 µl (1×); $MgCl_2$ (25 mmol/l): 3 µl (1.5 mmol/l); primer A (100 µmol/l): 1 µl (2 µmmol/l): primer B (100 µmmol/l): 1 µl (2 µmmol/l); template strand DNA; dNTP mixture (10 mmol/l): 1 µl (200 µmmol/l); polymerase: 1-2 µl (2-5 U); $H_2O$: ad 50 µl. PCR program: advance denaturing of 3-5 minutes at 95° C.; 32 cycles: denaturing 45 seconds at 95° C., hybridization for 45 seconds at variable temperature, elongation 0.5-1 min/1000 nt at 72° C., elongation 5 minutes at 72° C.; end: cooling at 12° C.

1.7 Result

Figure 7:
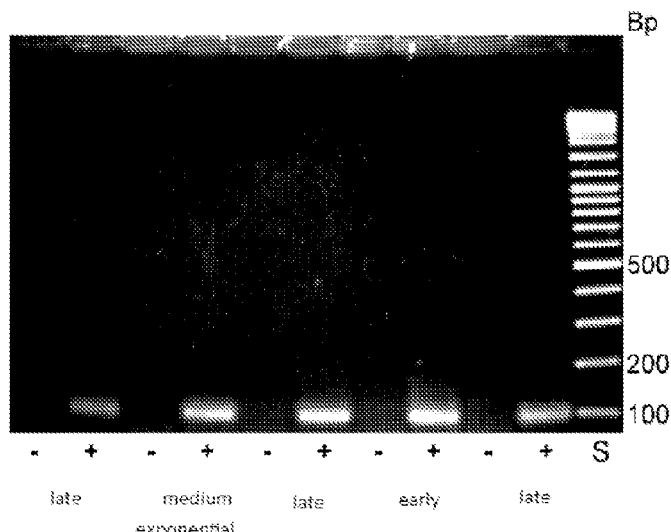
FIG. 7: Results of the qualitative RT PCR for analyzing transcripts of the solB gene: (−): negative control of the corresponding probe (replacement of the reverse transcriptase with water), (+): RT PCR of the corresponding probe, (S): order of magnitude (approximately 500 ng total RNA per RT PCR experiment)
Figure 8A:
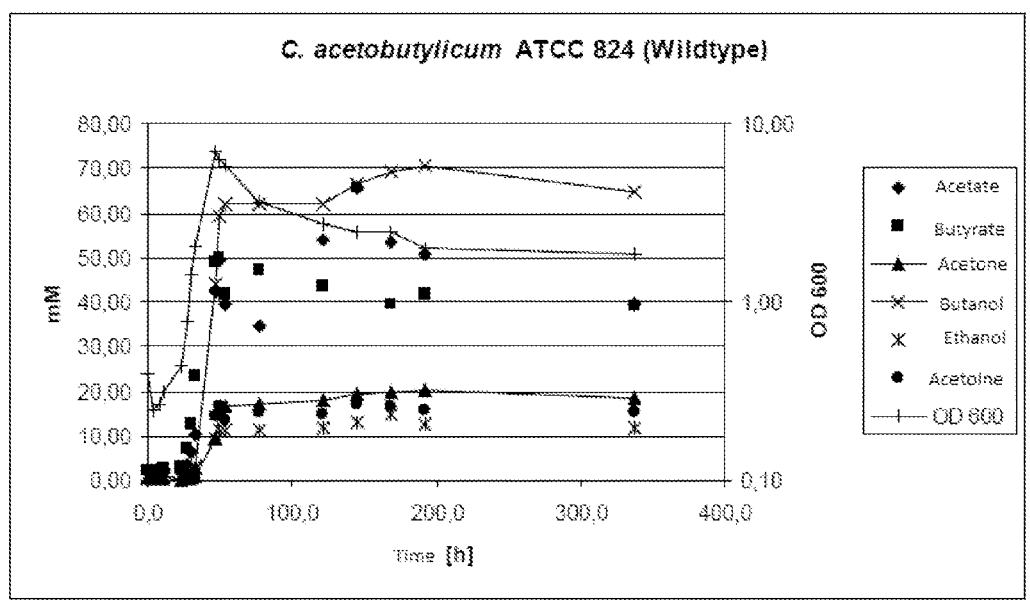
FIGS. 8A-C: Product spectra of the growth experiments of strain type C. acetobutylicum ATCC 824 (wild type) (FIG. 8A), a C. acetobutylicum pIMP1 mutant (FIG. 8B) and the C. acetobutylicum solB sense mutant (according to the invention, FIG. 8C) in phosphate-limited minimal medium; concentrations in mmol/l (mM)
Figure 8B:
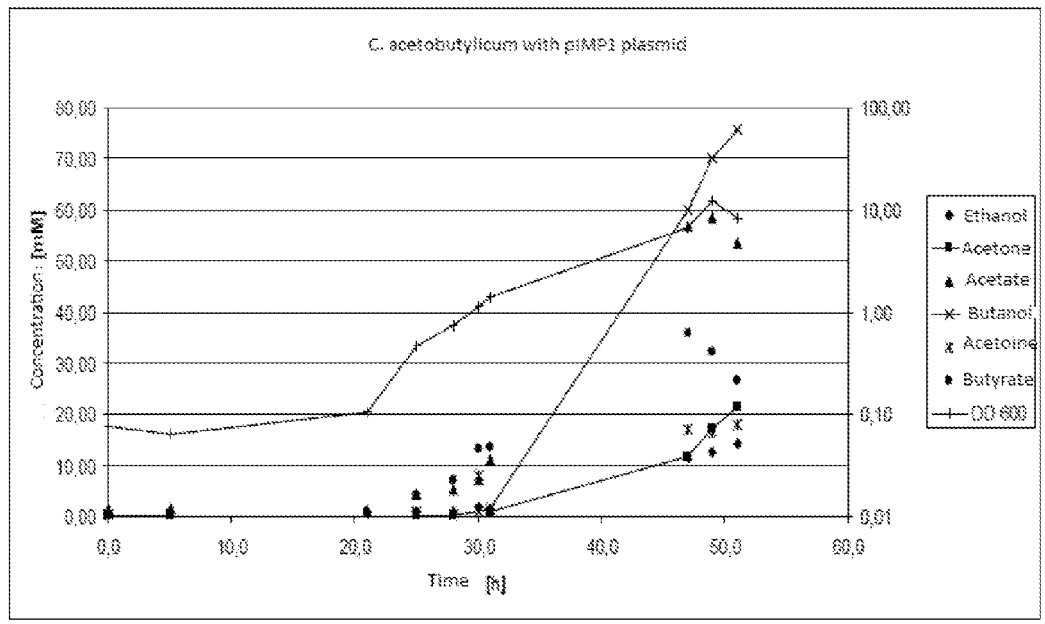
Figure 8C:
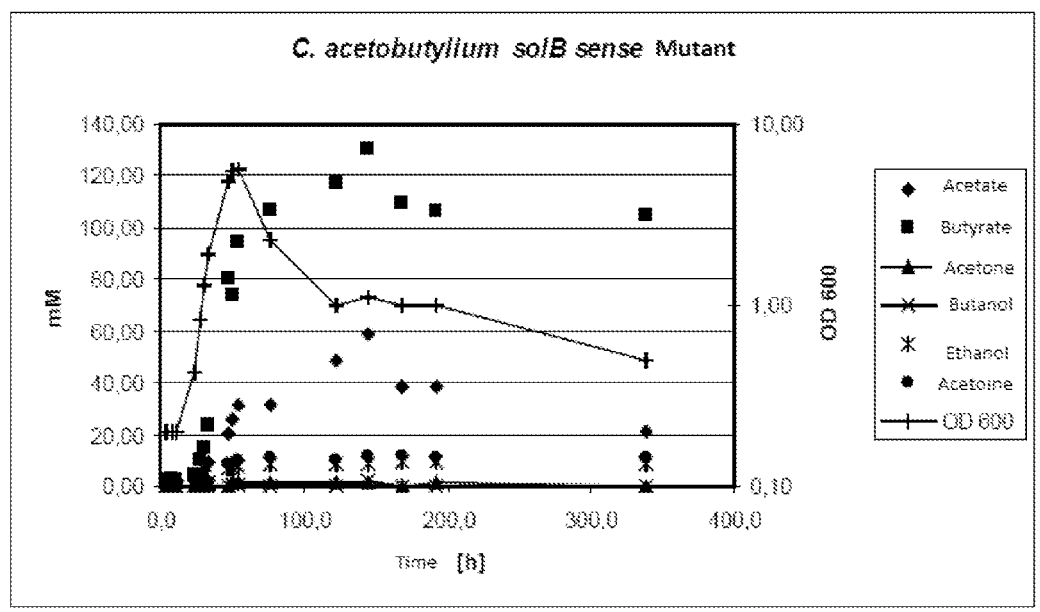
Figure 9A:
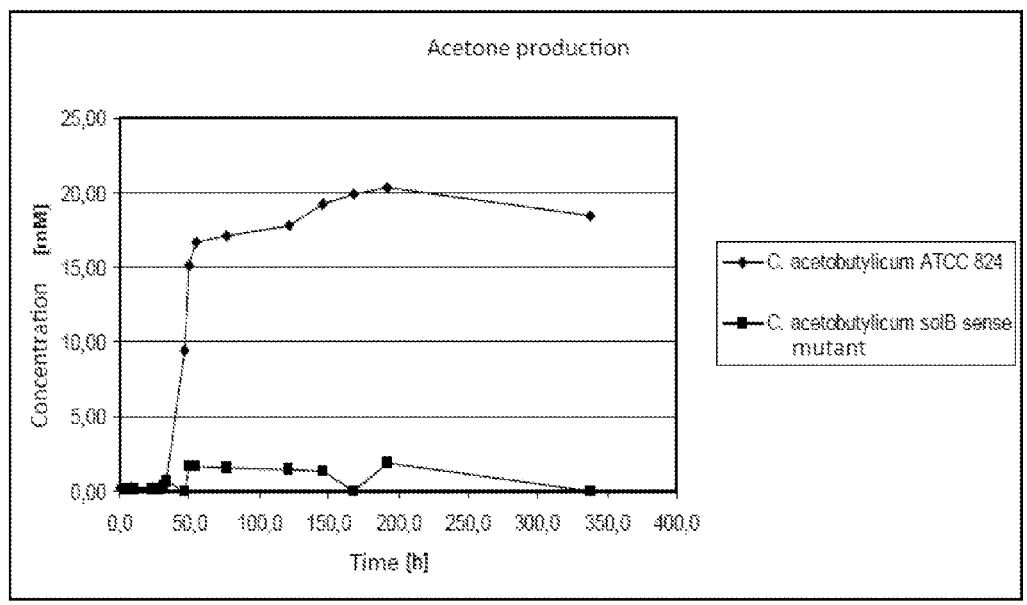
FIGS. 9A-B: Acetone production (FIG. 9A) and butanol production, (FIG. 9B) of strain type C. acetobutylicum ATCC 824 (wild type, FIG. 9A) and C. acetobutylicum solB sense mutant (according to the invention, FIG. 9B) on phosphate-limited minimal medium; concentrations in mmol/l (mM)
Figure 9B:
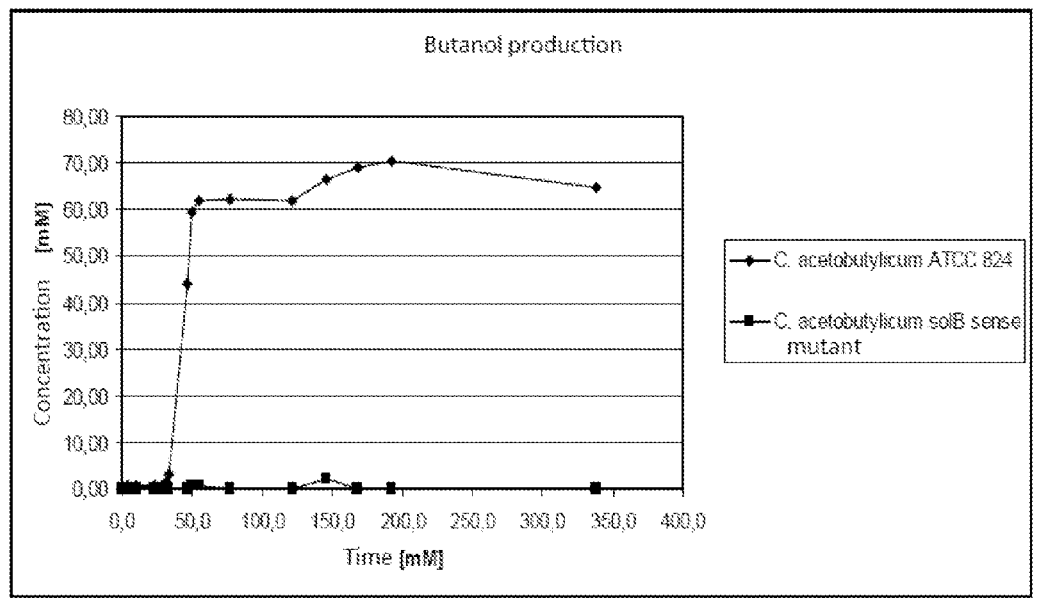
Figure 10A:
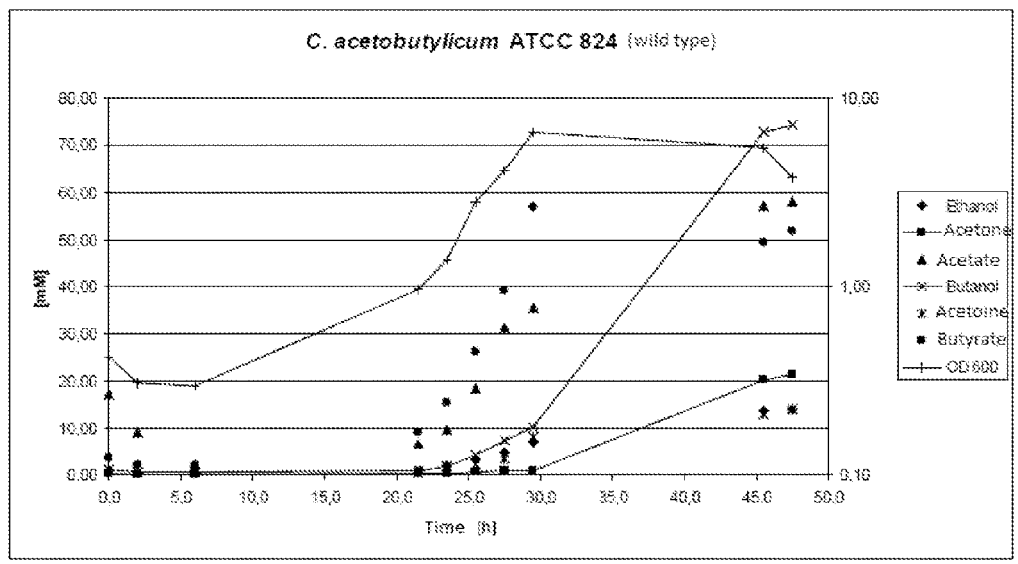
FIGS. 10A-D: Product spectra of the growth experiments of strain type C. acetobutylicum ATCC 824 (wild type, FIG. 10A), of a first C. acetobutylicum synthetic solB sense mutant (according to the invention, FIG. 10B), an additional C. acetobutylicum synthetic solB sense mutant (according to the invention, FIG. 10C) and still a further C. acetobutylicum synthetic solB sense mutant (according to the invention, FIG. 10D) in phosphate-limited minimal medium; concentrations in mmol/l (mM)
Figure 10B:
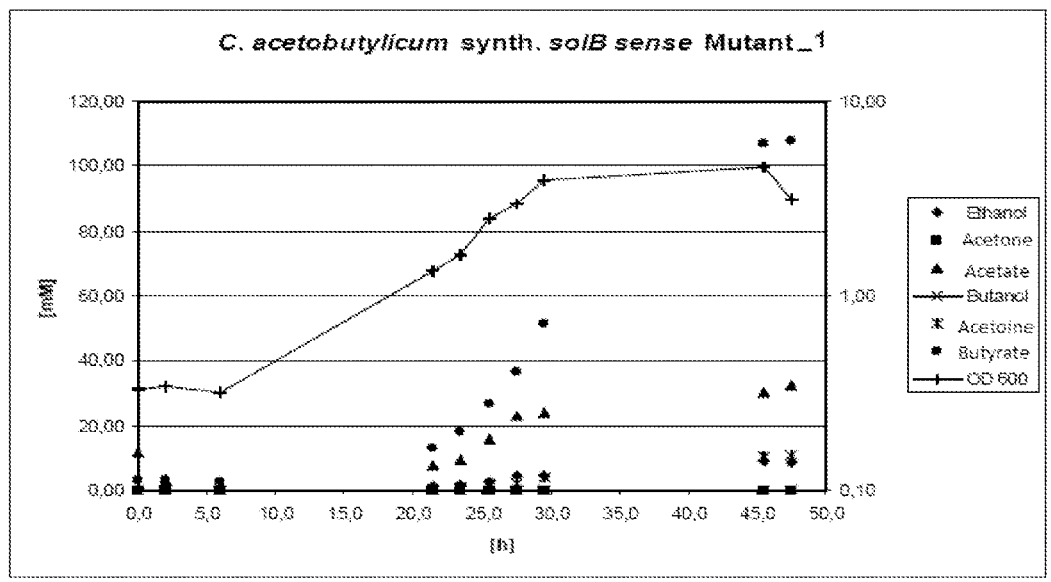
Figure 10C:
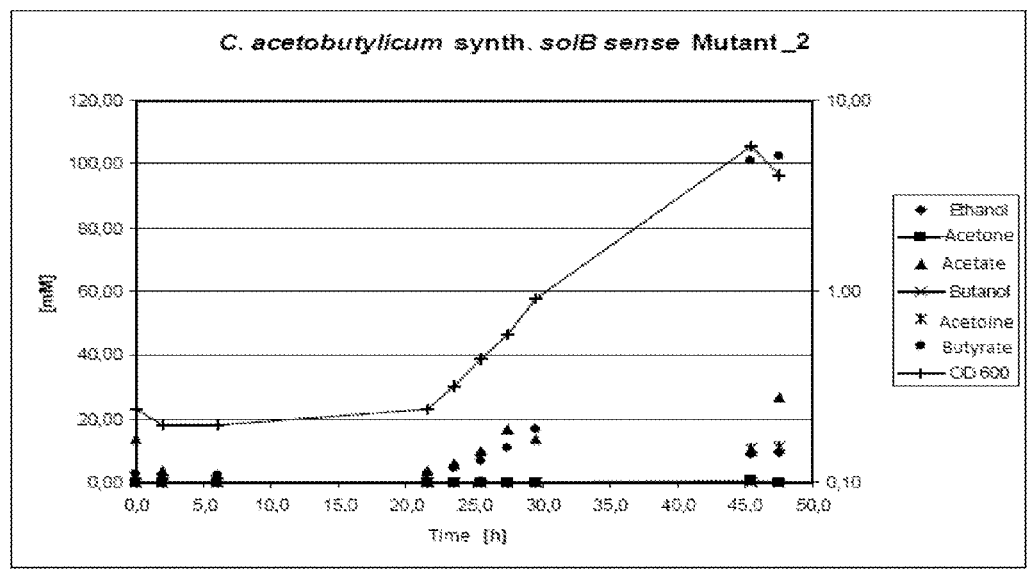
Figure 10D:
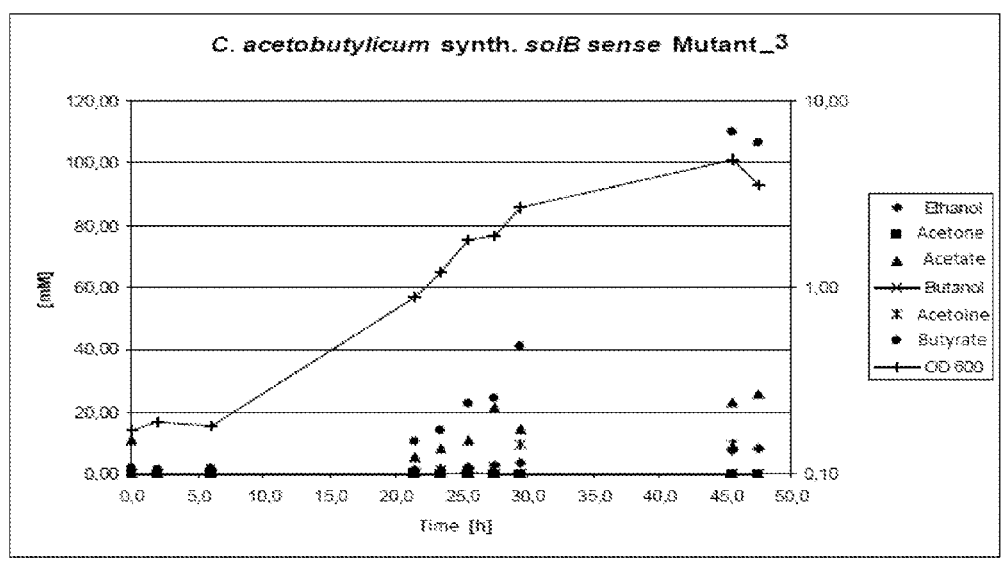
Figure 11A:
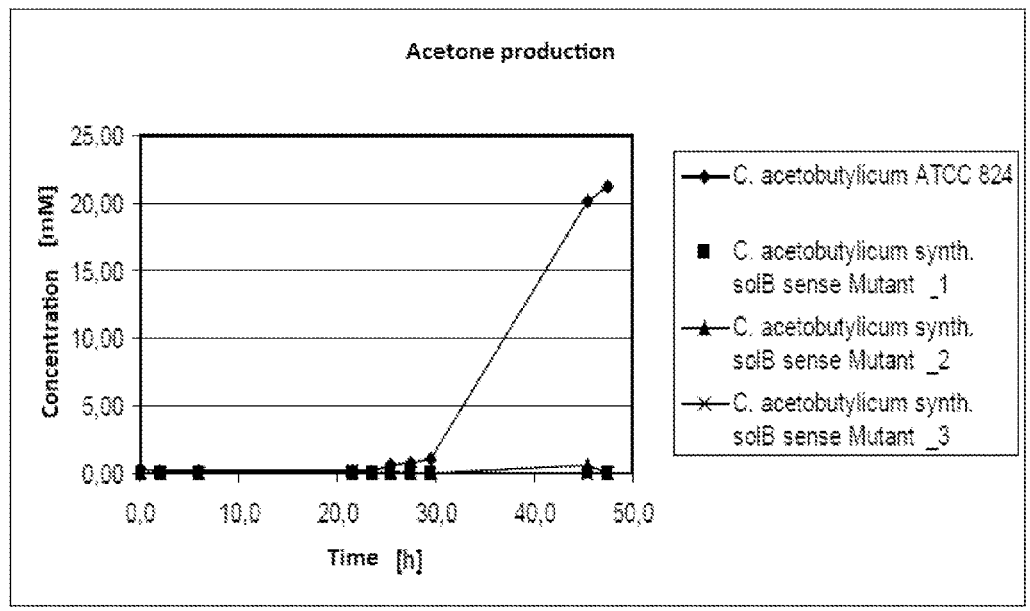
FIGS. 11A-B: Acetone production (FIG. 11A) and butanol production (FIG. 11B) of strain type C. acetobutylicum ATCC 824 (wild type), a first C. acetobutylicum synthetic solB sense mutant (according to the invention), a further C. acetobutylicum synthetic solB sense mutant (according to the invention) and a still further C. acetobutylicum synthetic solB sense mutant (according to the invention) on phosphate-limited minimal medium; concentrations in mmol/l (mM)
Figure 11B:
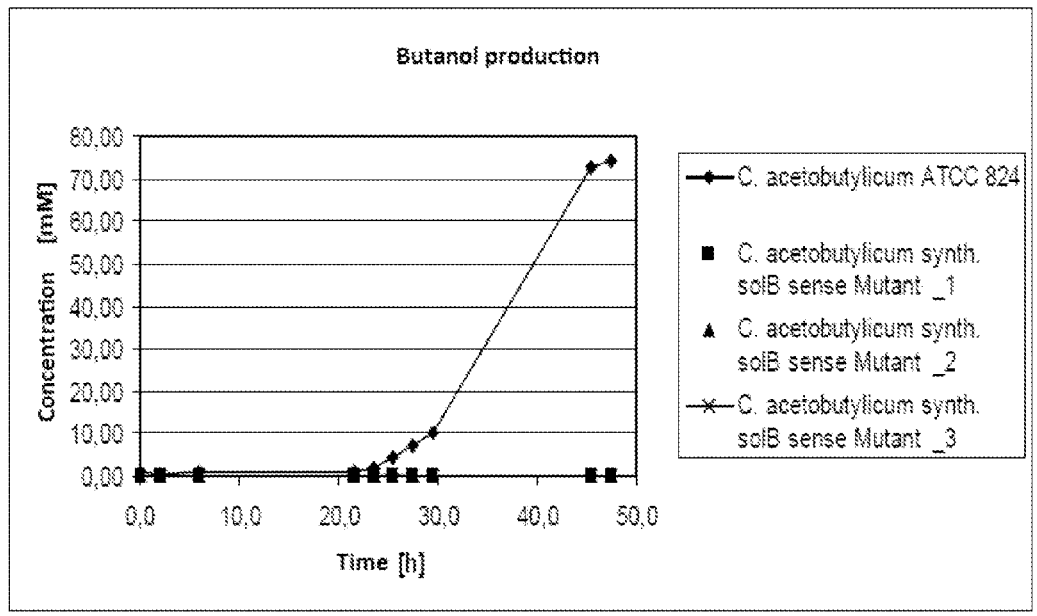

FIG. 7 shows the result of the qualitative RT PCR for analyzing the transcripts of the solB gene: (−): negative control of the respective probe (replacement of the reverse transcriptase with water), (+): RT PCR of the corresponding probe, (S): order of magnitude (approximately 500 ng total RNA per RT PCR experiment)

The potential promoter in the 5' region of the solB gene is active during the entire growth phase of strain C. acetobutylicum on phosphate-limited minimal medium, and specifically in the acid as well as in the solvent phase. The SolB (SolB-mRNA) can be verified in both phases, i.e. during the entire growth phase.

Example 2

Transformation of C. acetobutylicum

The following bacteria strains were used:
as host cell: *Clostridium acetobutylicum* ATCC 824 (strain type)
for methylation of plasmids: *E. coli* ER 2275 (trp-31, his-1, tonA2, rpsL104, supE44, xyl-7, mtl-2, metB1, e14-, Δ(lac)U169, endA1, recA1, R(zbgZ10::Tn10)Tcs, Δ(mcr-hsd-mrr)114:1510, [F', proAB, laclqZΔM15, zzd::mini, Tn10 (Kmr)])
for transformation: *E. coli* XL2-Blue (recA1, endA1, gyrA96, thi-1, hsdR17, supE44, relA1, lac, [F', proAB, laclqZΔM15, Tn10 (Tetr), amy, Camr]) and *E. coli* XL1-Blue MRF' (Δ(mcrΔ)183, Δ(mcrCB-hsdSMR-mrr)173, endA1, supE44, thi-1, recA1, gyrA96, relA1, lac, [F', proAB, laclqZΔM15, Tn10 (Tetr)])

The following plasmids were used:
pIMP1 (4.7 kbp) Emr, Apr, pMB1 on ColE1, ori(+) pIM13
As primer (oligodesoxy nucleotides) were used: SEQ ID NO: 11 to 16

2.1 Construction of Plasmids

Plasmid pIMP1 was selected as starting plasmid, the functionality of which could be shown without any doubt in C. acetobutylicum. Plasmid pIMP1 is a fusion consisting or E. coli cloning vector pUC18 and B. subtilis plasmid pIM13, the replication source of which and the MLSr resistance determinant (ermC) make the replication in, or clarithromycin resistance of, *C. acetobutylicum* possible. The number of copies of pIMP1 in this organism is 6-8 copies/cell.

Plasmids pBS1 to pBS17 were constructed according to the plasmid cards as per FIGS. 4 to 6. In the first step, the constitutively strong promoter of C. acetobutylicum phosphotransbutyrylase-butyratkinase(ptb-buk-) operon was amplified with the help of the oligonucleotides KL08 (SEQ ID NO: 11) and KL09 (SEQ ID NO: 12) in a standard PCR (see Example 1), with chromosomal DNA as template strand. Subsequent to EcoRI-NdeI digestion, this 123 bp fragment was ligated into correspondingly digested pIMP1 plasmid. Into the NdeI interface of the resulting pBS77, in a second step, the amplified and NdeI-digested promoter-less, total solB gene or 281 bp or antisense constructs thereof (see the following examples) that was ligated in a standard PCR with oligonucleotides sRNAshort_new_F (SEQ ID NO: 13) and sRNA_new_R (SEQ ID NO: 14) (see also Example 1) amplified and NdeI-digested promoter-less total so/8-Gen or 284 bp. Chromosomal DNA was the template strand for the standard PCR.

The correctness of the cloned sequences was inspected by sequencing (MWG). All plasmids were successfully methylated and transformed into C. acetobutylicum.

2.1.1 Electro Transformation of C. Acetobutylicum

To prepare the cells for electroporation, 5 ml CGM medium in Hungate tubules with approximately 50 µl spore suspension that was previously heated to 75° C., was inoculated and incubated by standing overnight at 37° C. 50 ml CGM medium was inoculated with the well-grown culture and incubated at 37° C. while standing until they had reached an OD600 of approximately 0.6 (logarithmically growing cells).

ETM buffer:

| Saccharose | 92.3 g | 270 mmol/l |
| $Na_2HPO_4 \times 2H_2O$ | 106.6 mg | 0.6 mmol/l |
| $NaH_2PO_4 \times 2H_2O$ | 686.6 mg | 4.4 mmol/l |
| $MgCl_2 \times 6H_2O$ | 2.04 g | 10 mmol/l |
| $H_2O$ | ad 1,000 ml | pH 6 |

ET buffer: corresponds to ETM buffer without $MgCl_2$

The following steps were performed in an anaerobic chamber: The cells were harvested by centrifuging (5,000 rpm, 10 minutes, 4° C.), the sediment was carefully suspended in cold ETM buffer and again centrifuged. Subsequently, the cell sediment was placed in 3 ml cold ET buffer and each 600 µl of cell suspension was transferred into a cooled electroporation cuvette (electrode distance 0.4 cm), in which previously plasmid DNA (3-15 µl, 1-10 µg) had been placed. DNA and Zellen were mixed by careful drawing up by using the pipette and the mixture was immediately electroporated. To generate the required voltage, a gene pulser II with pulse controller plus was used (from Bio-Rad Laboratories GmbH), whereby the following settings were selected: 1.8 kV; 50 µF; 600Ω. Under these conditions, the time constant was at 5-16 minutes. Subsequently, the cells were transferred into a Hungate tubules containing 1.4 ml CGM medium and incubated at least 4 hours at 37° C. Thereupon, 200-300 µl were spread on CGM plates with a corresponding antibiotic and/or used for inoculation of a corresponding selection medium.

2.1.2 Methylation of Plasmid DNA for the Transformation in C. Acetobutylicum

By having Cac824I, C. acetobutylicum has a type II restriction endonuclease, which recognizes and intersects the sequence motif 5'-GCNGC-3'. The methylation of the internal cytosine residue in the base sequences 5'-GCNGC-3' or 5'-GGCC-3' by the methyltransferase φ3TI of the B. subtilis phage φ3T leads to a prevention of the restriction by Cac824I. As it could be shown that the plasmid DNA that is methylated in such a way could be transferred into C. acetobutylicum at a transformation efficiency that was greater by two orders of magnitude than the corresponding un-methylated plasmid DNA, all plasmids constructed in this work that were to be transferred into C. acetobutylicum, were subjected to such a methylation.

The plasmids designated for electroporation in C. acetobutylicum were preferably methylated in vivo with the methyl transferase coded onto the plasmids pAN1 or pANS1. For this, E. coli strains ER2275 or XL1-Blue MRF' were used as they do not have any of the restriction systems McrA, McrBC and Mrr. These would intersect DNA, in which cytosine of the sequence 5'-CG-3' is methylated. Plasmids pAN1 or pANS1 were first established in these strains, and these were then transformed with the plasmid to be methylated. The p15A replication source of pAN1 or pANS1 was thereby compatible with the ColE1 replicon. All plasmids constructed for the purpose of the transformation of C. acetobutylicum of this work carried this replicon.

The plasmid DNA modified in this way was isolated by means of mini-preparations from the E. coli strains. Thereby, plasmids pAN1 and pANS1 did not have to be separately removed from the plasmid preparations, as they do not replicate in C. acetobutylicum. It was possible to inspect the successful methylation by restriction with Fnu4HI or SatI, methylation-sensitive isoschizomers of Cac8241.

2.1.3 Transformation of E. coli

For the transformation in E. coli, strains E. coli XL1-Blue MRF' and XL2-Blue were used, as they have a high degree of transformation efficiency.

2.1.3.1 Chemical Transformation of E. Coli

For producing cold-competent cells of E. coli, first a strain culture was spread on an LB plate with a corresponding antibiotic for selection and incubated overnight at 37° C. Subsequently, a single colony was transferred in 5 ml LB medium with antibiotic and again incubated overnight at 37° C. while shaking. This pre-culture was used as inoculum for the main culture, 250 ml SOB medium with an antibiotic. At 18° C., the culture was shaken until an $OD_{600}$ of 0.5-0.6 (approximately 12-20 hours) was obtained. The cells were incubated for 10 minutes on ice and harvested by centrifugation (5,000 rpm, 10 min, 4° C.). The cell sediment was washed in 80 ml of ice-cold PIPES buffer, incubated for 10 minutes on ice and again centrifuged as described. Subsequently, the sediment was dissolved in 20 ml PIPES buffer and slowly, during a 10-minute incubation on ice, reacted with DMSO (1.5 ml, corresponds to an end concentration of 7%, v/v). Aliquots of 200 µl were pipetted into pre-cooled 1.5 ml reaction vessels and immediately shock-frozen in liquid nitrogen. At −70° C., the cells could be stored without any obvious worsening of the transformation efficiency.

For transformation, the corresponding number of aliquots (200 µl/transformation) was defrosted on ice and plasmid DNA or ligation mixture (up to 20 µl) was added by pipette. After an incubation of 30-40 minutes on ice, the cells were exposed to a one-minute heat shock at 42° C., briefly cooled on ice and reacted with 800 µl LB medium. Immediately thereafter, incubation at 37° C., while shaking slightly for 45-60 minutes. In the case of the transformation of plasmids, 20-50 µl of the mixture was spread on plates with corresponding selection medium. If the transformation occurred with ligation mixture, the mixture was centrifuged (1,000 rpm, 30 seconds, RT), 850 µl of the supernatant was discarded, the cells in the remaining 150 µl of medium were suspended and then spread out on plates in their entirety onto selection medium.

2.1.3.2 Elektroporation of E. Coli

By using electroporation, DNA can, compared to artificially induced transformations, be transferred with higher efficiency. For producing electro-competent E. coli cells, 250 ml LB medium was inoculated with the overnight pre-culture of a corresponding strain and incubated while shaking up to an OD600 of 0.6-0.8 at 37° C. Upon reaching the desired $OD_{600}$ the culture was cooled for 15 minutes on ice and the cells subsequently harvested by centrifugation (5,000 rpm, 10 minutes, 4° C.). The sediment was washed 2× with 250 ml ice-cold water and twice in 10-30 ml ice-cold glycerin (10%, v/v). Finally, the cell sediment was placed in 1 ml ice-cold glycerin (10%, v/v) and the cell suspension used either immediately for electroporation or shock-frozen in liquid nitrogen in 50 µl aliquots. At −70° C., the cells could be stored up to three months.

For the electroporation, a corresponding amount of aliquots (50 µl per transformation) was defrosted on ice and pipetted into a suitable, ice-cooled, sterile electroporation cuvette (electrode distance: 0.2 cm). In order to transform intact plasmids, 100 pg plasmid DNA was used in the electroporation of E. coli ER2275 [pAN1] cells 1 µg plasmid DNA. Ligation mixtures had to be dialyzed before the transformation if more than 100 ng DNA was used per transformation experiment. The DNA was added to the cells on ice and the mixture was immediately electroporated. To generate the required voltage, a gene pulser II with pulse controller plus (from Bio-Rad Laboratories GmbH) was used, settings: 2.5 kV; 25 µF; 200Ω. The time constant was between 4.6 and 4.9 minutes. After the pulse, 1 ml LB medium was added to the mixture immediately, the cell suspension was transferred into a 1.5 ml reaction vessel and it was incubated while shaking for 1 hour 37° C. Aliquots of 100-250 µl were subsequently spread on plates with LB selection medium.

2.1.4 Plasmid Preparation from E. Coli

The "peqGOLD plasmid miniprep" was used to isolate pure plasmid DNA in a short time. To do so, approximately 4 ml E. coli was placed in culture overnight (resulted in approximately 10 µg plasmid DNA, depending on the E. coli strain used). The precise execution of the steps involved was performed according to the instructions provided by the manufacturer.

2.1.5 Purification of DNA

For purifying the DNA, the "UltraClean™15 Kit" was used. The process was performed according to the instructions provided by the manufacturer.

2.1.6 Restriction Splitting of DNA

Restricted digestion of DNA for analytic and preparative purposes occurred as per the recommendations of the manufacturers at a volume of 10-200 µl at 37° C., most of the time for 1 hour.

The reaction could be stopped by inactivation of heat (dependent on the enzyme, according to information provided by the manufacturer), phenol/chloroform extraction or purification with the "UltraClean15 Kit" (from Fermentas). In the case of multiple restrictions, a buffer system was used in which all enzymes showed at least 50-100% activity. If such a buffer system was not available, the mixture was re-buffered between the individual restriction digestions. Additionally, in the digestion of PCR fragments, the fact must be considered that restriction enzymes require, as a rule, a certain excess of nucleotide, in order to be able to cut efficiently. For this reason, in the production of those PCR fragments, that had interfaces at the end of the DNA strand, it was ensured that a nucleotide excess of 5-8 bases was generated. Per 1 µg DNA, approximately 10 U or at least 10 U of the restriction enzyme was used. 1 U is defined as that amount of enzyme that is required in order to completely split 1 µg λ-DNA at 37° C. in 60 minutes. The restriction digestion was inspected with an agarose gel electrophoresis.

2.1.7 Dephosphorylation of DNA Fragments

In order to prevent the re-ligation of the vector in a ligation, after a restriction digestion, the phosphate residues at the 5' ends were hydrolyzed. Thereby, "Shrimp Alkaline Phosphatase" (SAP; from Fermentas) was used. The dephosphorylation was performed according to the information provided by the manufacturer, as a rule, directly in the restriction mixture. For this, the 20-100 µl restricting mixture was mixed with 2 U SAP incubated for 30 minutes at 37° C., and subsequently inactivated for 15 minutes at 65° C.

2.1.8 Ligation of DNA Fragments (According to Weiss et al, 1968)

Ligations were performed with 20 µl mixtures. Thereby, as a rule, a molar relationship of vector to insert of 1:3 to 1:5 was aimed for.

Water and DNA were first pre-incubated for 5 minutes at 55° C. and only after cooling to the final incubation temperature, the mixture was complemented with 2 µl 10× ligase buffer and 1-2 U T4-DNA ligase (from Fermentas). The mixture was then either incubated for 1 hour at 22° C. or 12 hours at 16° C. The ligation mixture was subsequently transformed directly into E. coli.

2.1.9 Isolation of Total DNA

First, 5 ml CGM overnight culture was centrifuged (5,000 rpm, 10 minutes 4° C.). After washing with 1 ml KP buffer (10 mmol/l, pH 7.5) the cell sediment was dissolved in 500 µl KP buffer and transferred into a reaction vessel. Cell disruption and the simultaneous digestion of undesired RNA occurred by adding 10 mg lysozyme (100,000 U/mg), 5 µl RNase A 10 mg/ml (from Fermentas) and an incubation of 1 hour at 37° C. Thereafter, a sequential addition of 50 µl of a 10% (w/v) SDS and 30 µl of a proteinase K solution was followed with a subsequent incubation of 1 hour at 55° C. A phenol/chloroform extraction followed and an ethanol precipitation. The dried DNA was dissolved in approximately 300 µl $H_2O$ and stored at 4° C.

Proteinase K solution: 20 mg/ml proteinase K (Roche Diagnostics GmbH) in 50% glycerin (v/v)

2.2 Cultivation and Product Spectrum

Anaerobic growth of C. acetobutylicum was cultivated at volumes up to 5 ml in Hungate tubules (Bellco Glass Inc.; Vineland; USA) with butyl stoppers and screw covers. Larger volumes were cultivated in 125-ml-, 500-ml and 1000 ml Müller-Krempel flasks (Müller & Krempel, Bülach, Switzerland) with natural rubber stoppers and stainless steel covers. Because of the strong gas development due to C. acetobutylicum ($H_2$ and $CO_2$), the vessels were only filled up to half of the volume and upon entering the logarithmic growth phase, provided with a cannula, through which excess gas could escape.

2.2.1 Measurement of Cloudiness

The growth progression of the bacteria culture was tracked with the help of a spectral photometer at a wavelength of 600 nm using the increasing optical density (OD). The measurement took place in a 1 ml half micro cuvette (layer thickness 1 cm) with corresponding medium as reference value. To guarantee linearity between the increase of the extinction and the number of cells, the probes were diluted with medium starting at absorption measurement values of 0.4.

2.2.2 Measurement of the External pH Value

To determine the pH value of culture supernatants, a precision pH meter was used. To avoid contamination of the measurement electrode, the culture was centrifuged (10,000 rpm, 10 minutes, room temperature) and the supernatant transferred to a test tube.

2.2.3 Gas Chromatography Analysis of the Synthesized Products

To record the product spectrum of the strains in culture, respectively 2 ml culture supernatant was centrifuged (10,000 rpm, 10 min, RT) and 1 ml thereof was transferred to a roll-edged vessel. As internal standard, 100 µl of a 110 mmol/l isobutanol solution, dissolved in 2 N (2 mol/l) hydrochloric acid was added to each probe and it was closed gas-tight with a septum. Processed in this way, the probes were analyzed in the gas-phase chromatograph under the following conditions:

Parameters of the GC measurement:
Column: glass, packed, ID 2 mm
Column material: chromosorb 101 with 80 to 100 mesh
Injector temperature: 195° C.
Detector: FID, 230° C.
Carrier gas: $N_2$ (15 ml/min)
FID gasses: $H_2$ (30 ml/min)
"Make-up" gas: $N_2$ (15 ml/min)
Synthetic air
(80% $N_2$, 20% $O_2$): 250 ml/min
Probe volume: 1 µl; "hot needle" injection
Temperature profile:
130° C. for 1 min; 130° C. to 150° C. with 4° C./min; 150° C. to 160° C. with 5° C./min; 160° C. to 180° C. with 7° C./min; 180° C. to 200° C. with 10° C./min; 200° C. for 3 min The analysis was performed using a Maestro Sampler II Version 2.5 (Chrompack). To make a quantification of the probes possible, calibration runs were performed with acetate, acetoine, acetone, butanol, butyrate and ethanol at a concentration of 5 mmol/l. The automatic analysis was based on a calibrated peak surface calculation and internal standards.

Example 3

Separate Synthesis of the SolB Transcript and Insertion of this Transcript into Clostridia In a chemical synthesis, an RNA fragment of the SolB transcript (SolB-mRNA) was artificially synthesized. This RNA molecule was inserted into the wild type clostridia by means of electroporation (see Example 2). The clostridia treated in this way were cultivated according to Example 2, and the product spectrum was analyzed.

Example 4

Product Spectra of Strains *C. Acetobutylicum* pIMP1 and *C. Acetobutylicum* solB Sense With strain type *C. acetobutylicum* ATCC 824 (wild type), of *C. acetobutylicum* pIMP1 mutant and *C. acetobutylicum* solB sense mutant according to the invention, growth experiments were performed in 50 ml phosphate-limited minimal medium.

4.1 Experiments

Mutant *C. acetobutylicum* pIMP1 carries vector pIMP1 without solB construct. This strain is the control.

Mutant *C. acetobutylicum* solB sense carries the plasmid pBS1. The plasmid was constructed on the basis of vector pIMP1. This vector was provided with constitutive ptb-buk promoter (promoter of phosphotransbutyrylase-butyratkinase operon). Behind the promoter, the promoter-less solB gene was cloned in sense orientation. The vector card is shown in FIG. 3.

4.2 Results

All three strains grew identically. FIGS. 8A to 8C show the product spectra of the growth experiments of strain type *C. acetobutylicum* ATCC 824 (wild type), FIG. 8A, of a *C. acetobutylicum* pIMP1 mutant, FIG. 8B, and of *C. acetobutylicum* solB sense mutant (according to the invention), FIG. 8C, in phosphate-limited minimal medium; concentrations in mmol/l (mM). FIGS. 9A and 9B show the acetone production, FIG. 9A, and butanol production, FIG. 9B, of strain type *C. acetobutylicum* ATCC 824 (wild type), FIG. 9A, and the *C. acetobutylicum* solB sense mutant (according to the invention), FIG. 9B, on phosphate-limited minimal medium; concentrations in mmol/l (mM).

Strain type *C. acetobutylicum* ATCC 824 (wild type) and *C. acetobutylicum* pIMP1 mutant (control) produced on average a maximum of approximately 15 mmol/l acetone and approximately 70 mmol/l butanol. The plasmid construct pIMP1 does not have a detectable influence on the product spectrum of the host cell.

The *C. acetobutylicum* solB sense mutant produces approximately 2 mmol/l acetone and approximately 2 to 15 mmol/l butanol. It produces approximately 90% less acetone and butanol than strain type *C. acetobutylicum* ATCC 824 (wild type).

Example 5

Product Spectra of *C. Acetobutylicum* Synthetic SolB Sense Mutants

With strain type *C. acetobutylicum* ATCC 824 (wild type) and *C. acetobutylicum* synthetic solB sense mutant according to the invention, growth experiments were performed in 50 ml phosphate-limited minimal medium.

5.1 Experiments

Mutant *C. acetobutylicum* synthetic solB sense carries the plasmid pBS7. The plasmid was constructed on the basis of the pIMP1 vector. The solB gene was cloned with its own promoter into the multiple cloning site of vector (BamHI and EcoRI). The vector card is shown in FIG. 4.

5.2 Results

All strains grew identically.

FIGS. 10A to 10C show the product spectra of the growth experiments of strain type *C. acetobutylicum* ATCC 824 (wild type), FIG. 10A, of a first *C. acetobutylicum* synthetic solB sense mutant (according to the invention), FIG. 10B, of an additional *C. acetobutylicum* synthetic solB sense mutant (according to the invention), FIG. 10C, yet a further *C. acetobutylicum* synthetic solB sense mutant (according to the invention), FIG. 10D, in phosphate-limited minimal medium; concentrations in mmol/l (mM).

FIGS. 11A and 11B show the acetone production, FIG. 11A, and butanol production, FIG. 11B, of strain type *C. acetobutylicum* ATCC 824 (wild type), of a first *C. acetobutylicum* synthetic solB sense mutant (according to the invention), a further *C. acetobutylicum* synthetic solB sense mutant (according to the invention) and yet an additional *C. acetobutylicum* synthetic solB sense mutant (according to the invention) on phosphate-limited minimal medium; concentrations in mmol/l (mM).

Strain type *C. acetobutylicum* ATCC 824 (wild type) produces on average approximately 15 mmol/l acetone and approximately 70 mmol/l butanol. All *C. acetobutylicum* synthetic solB sense mutants produce almost no acetone and butanol any more.

Example 6

Product Spectra of *C. Acetobutylicum* Synthetic SolB Antisense Mutants

With strain type *C. acetobutylicum* ATCC 824 (wild type) and mutant *C. acetobutylicum* synthetic solB antisense according to the invention, growth experiments were performed in 50 ml phosphate-limited minimal medium.

6.1 Experiments

Mutants *C. acetobutylicum* synthetic solB antisense carry the plasmid pBS13. The plasmid was designed on the basis of the pIMP1 vector. The promoter and the terminator of the solB gene were cloned in sense orientation, the rest of the solB gene (137 bp) as well as in the other vectors, fragments of the solB Gens (3'solB 75 bp (pBS14), 3'solB 115 bp, (pBS15), 5'solB 72 bp (pBS16), 5'solB 102 bp (pBS17), were cloned intermediately in antisense orientation. The vector cards are shown in FIGS. 5 and 6A to 6D.

6.2 Results

All strains grew identically.

Strain type *C. acetobutylicum* ATCC 824 (wild type) produces approximately 15 mmol/l acetone and approximately 70 mmol/l butanol; mutant *C. acetobutylicum* synthetic solB antisense and mutant *C. acetobutylicum* synthetic solB antisense X bp (X=3'-solB 75 bp; 3'-solB 115 bp; 5'-solB 72 bp; 5' solB 102 bp), produce approximately 30% more butanol than strain type *C. acetobutylicum* ATCC 824 (wild type).

Example 7

Production of Acetate and Butyrate

Figure 12A:
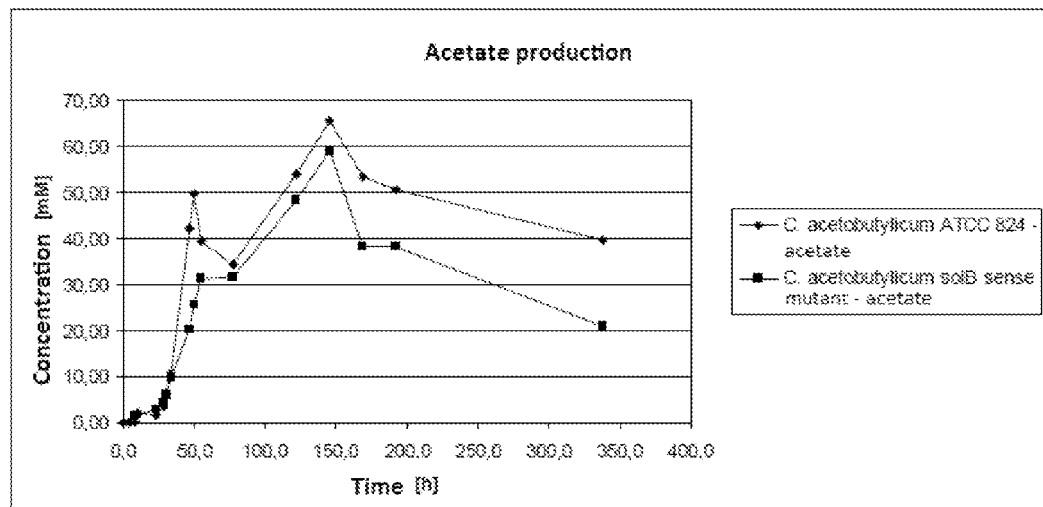
FIGS. 12A-B: Acetate production (FIG. 12A) and butyrate production (FIG. 12B) of strain type C. acetobutylicum ATCC 824 (wild type) and C. acetobutylicum solB sense mutant (according to the invention) on phosphate-limited minimal medium; concentrations in mmol/l (mM)
Figure 12B:
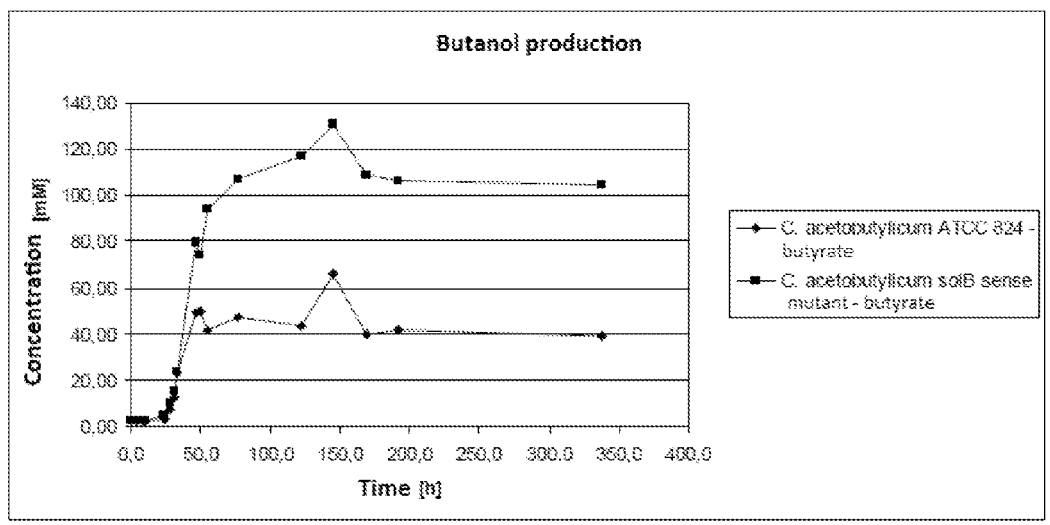

The cultivation of cells was performed according to the preceding examples. FIG. 12A shows the acetate production and FIG. 12B the butyrate production of strain type *C. acetobutylicum* ATCC 824 (wild type) and a *C. acetobutylicum* solB sense mutant (according to the invention) on phosphate-limited minimal medium; concentrations in mmol/l (mM). The cultivation of cells was performed according to the preceding examples.

Strain type *C. acetobutylicum* ATCC 824 (wild type) produces up to approximately 66 mmol/l acetate, mutant *C. acetobutylicum* solB sense according to the invention produces a maximum of approximately 60 mmol/l acetate. Strain type *C. acetobutylicum* ATCC 824 (wild type) produces up to approximately 50 mmol/l butyrate, a mutant *C. acetobutylicum* solB sense according to the invention produces approximately 105 mmol/l butyrate. Mutant *C. acetobutylicum* solB sense according to the invention produces approximately twice as much butyrate as the wild type.

Figure 13A:
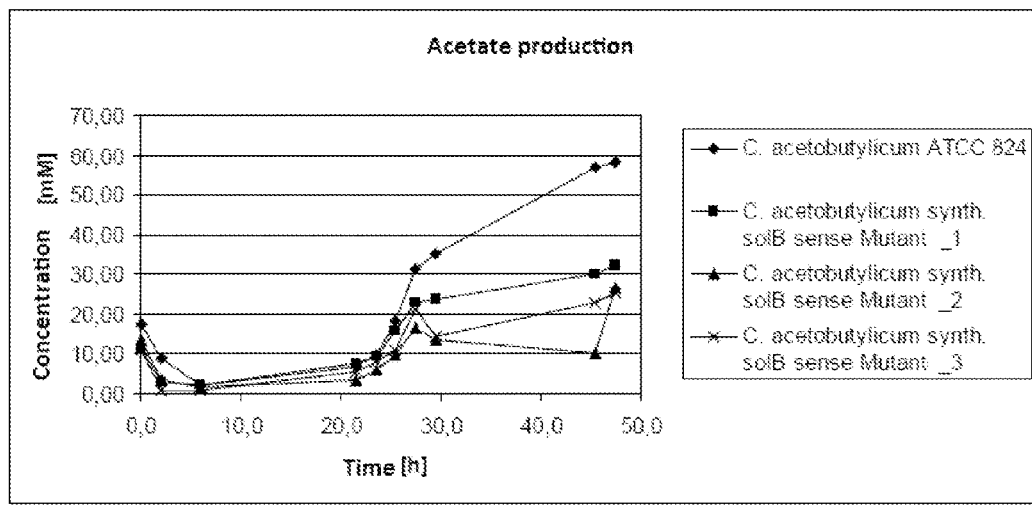
FIGS. 13A-B: Acetate production (FIG. 13A) and Butyrate production (FIG. 13B) of strain type C. acetobutylicum ATCC 824 (wild type) and the C. acetobutylicum synthetic solB sense mutants (according to the invention) on phosphate-limited minimal medium; concentrations in mmol/l (mM)
Figure 13B:
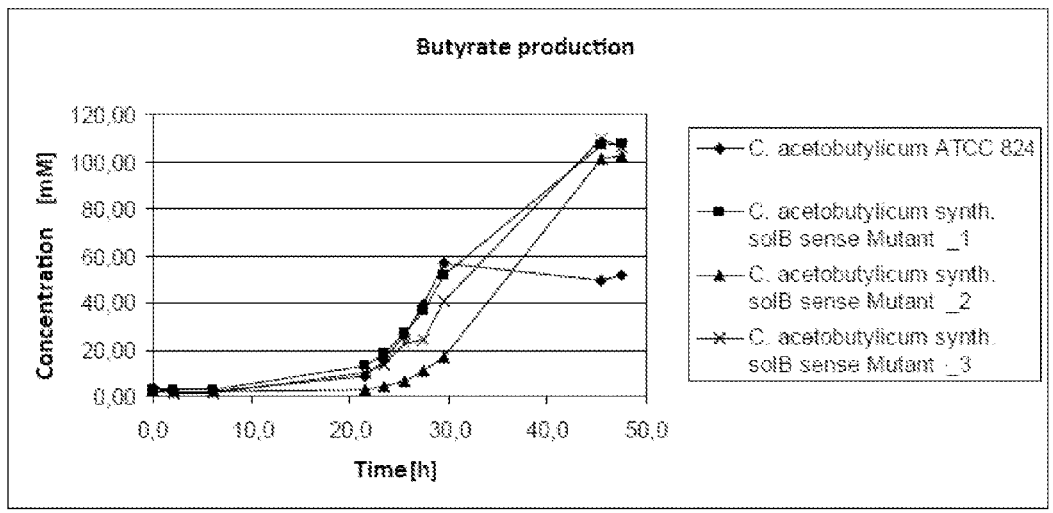

FIG. 13A shows the acetate production and FIG. 13B the butyrate production of strain type *C. acetobutylicum* ATCC 824 (wild type) and of three *C. acetobutylicum* synthetic solB sense mutants (according to the invention) on phosphate-limited minimal medium; concentrations in mmol/l (mM). The cultivation of the cells took place according to the preceding examples.

Strain type *C. acetobutylicum* ATCC 824 (wild type) produces up to approximately 55 mmol/l acetate here, mutants *C. acetobutylicum* synthetic solB sense according to the invention, produce up to approximately 30 mmol/l acetate. Strain type *C. acetobutylicum* ATCC 824 (wild type) produces up to approximately 50 mmol/l butyrate, mutants of *C. acetobutylicum* synthetic solB sense according to the invention, produce approximately 105 to 110 mmol/l butyrate. Mutants *C. acetobutylicum* synthetic solB sense according to the invention produce approximately twice as much butyrate as the wild type.

LITERATURE

Fischer, R.-J., J. Helms and P. Dürre. 1993. Cloning, sequencing and molecular analysis of the sol operon of *Clostridium acetobutylicum*, a chromosomal locus involved in solventogenesis. J. Bacteriol. 175: 6959-6969.

Nair, R. V, Green, E. M., Watson, D. E., Bennett, G. E. and Papoutsakis, E. T. 1999. Regulation of the sol locus genes for butanol and acetone formation in *Clostridium acetobutylicum* ATCC 824 by a putative transcriptional repressor. J. Bacteriol. 181: 319-330.

Thormann, K., L. Feustel, K. Lorenz, S, Nakotte and P. Dürre. 2002. Control of butanol formation in *Clostridium acetobutylicum* by transcriptional activation. J. Bacteriol. 184: 1966-1973.

---

The invention claimed is:

1. An isolated nucleic acid molecule suitable for modulating the expression of at least one enzyme activity of a sol operon or an adc operon for solvent and/or acid production in a host cell, the molecule having a nucleic acid sequence selected from the group consisting of:
  a) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10,
  b) sequences fully complementary thereof; and
  c) modified sequences and fragments that have—with the sequences according to (a) or (b)—at least 90% sequence congruence and code the function of a regulator for modulating the expression of this enzyme activity.

2. The nucleic acid molecule according to claim 1, which is an RNA molecule.

3. The nucleic acid molecule according to claim 2, whereby the modulation of the enzyme activity occurs by the regulation of at least one process selected from: transcription of a gene that is coding the enzyme activity, and translation of the gene transcript, whereby the nucleic acid molecule attaches to at least one structure mediating the process and modulates its function.

4. An isolated nucleic acid molecule that is a genetic mutant of the nucleic acid molecule according to claim 1, whereby at least one genetic mutation is selected from the group consisting of: inversion, deletion and insertion of at least one nucleotide.

5. The nucleic acid molecule of claim 1, wherein at least one expressible copy of the nucleic acid molecule is contained within a vector.

6. The vector according to claim 5, in which the nucleic acid molecule is located expressible in sense orientation.

7. The vector according to claim 6, in which the nucleic acid molecule is located expressible in antisense orientation.

8. An isolated RNA molecule for modulating the expression of at least one enzyme activity of a sol operon or an adc operon for acid and/or solvent production in a host cell, whereby the molecule is selected from the group consisting of:
  a) an RNA molecule which is transcribable out of the nucleic acid molecule according to claim 1; and
  b) fragments of (a), which have the function of a regulator for modulating the expression of this enzyme activity in the host cell.

9. The nucleic acid molecule of claim 1, wherein the nucleic acid molecule is contained within a genetically modified host cell, the host cell containing the nucleic acid molecule as a heterologous gene.

10. The vector of claim 5, wherein the vector is contained within a genetically modified host cell.

11. The RNA molecule of claim 8, wherein the RNA molecule is contained in a host cell.

12. The nucleic acid molecule of claim 1, wherein the nucleic acid molecule is contained within a genetically modified host cell, in which the expression of the nucleic acid molecule is inhibited or prevented.

13. The genetically modified host cell according to claim 10, which is a knock-out mutant of the gene solB and/or of a homolog or ortholog of such.

14. A method for the production of a genetically modified host cell with modified acid and/or solvent production containing the step:
  genetically modifying the host cell with a vector including at least one expressible copy of a nucleic acid molecule having a nucleic acid sequence selected from the group consisting of:
  a) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10,
  b) sequences fully complementary thereof; and
  c) modified sequences and fragments that have—with the sequences according to (a) or (b)—at least 90% sequence congruence and code the function of a regulator for modulating the expression of this enzyme activity; or
  transferring an RNA molecule into a host cell, the RNA molecule selected from the group consisting of:
  a) an RNA molecule transcribable out of the nucleic acid molecule; and
  b) fragments of (a), which have the function of a regulator for modulating the expression of this enzyme activity in the host cell.

15. The method according to claim 14, whereby the host cell is genetically modified so that the nucleic acid molecule is expressed in sense orientation.

16. The method according to claim 14, whereby the host cell is genetically modified so that the nucleic acid molecule is expressed in antisense orientation.

* * * * *